US009441032B2

(12) United States Patent
Warter et al.

(10) Patent No.: US 9,441,032 B2
(45) Date of Patent: Sep. 13, 2016

(54) BINDING MOLECULES AGAINST CHIKUNGUNYA VIRUS AND USES THEREOF

(75) Inventors: Lucile Warter, Singapore (SG);
Jean-Pierre Abastado, Singapore (SG);
Alessandra Nardin, Singapore (SG);
Cheng-I Wang, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 251 days.

(21) Appl. No.: 13/639,850

(22) PCT Filed: Apr. 7, 2011

(86) PCT No.: PCT/EP2011/055402
§ 371 (c)(1),
(2), (4) Date: Mar. 22, 2013

(87) PCT Pub. No.: WO2011/124635
PCT Pub. Date: Oct. 13, 2011

(65) Prior Publication Data
US 2013/0189279 A1    Jul. 25, 2013

(30) Foreign Application Priority Data

Apr. 7, 2010   (EP) .................................. 10305353
Apr. 7, 2010   (SG) ................................ 201002413

(51) Int. Cl.
A61K 38/00    (2006.01)
C07K 14/005   (2006.01)
C07K 16/10    (2006.01)
G01N 33/569   (2006.01)

(52) U.S. Cl.
CPC ........... C07K 16/1081 (2013.01); A61K 38/00 (2013.01); C07K 14/005 (2013.01); G01N 33/56983 (2013.01); C07K 2317/21 (2013.01); C07K 2317/76 (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,740,461 | A | 4/1988 | Kaufman |
| 4,816,397 | A | 3/1989 | Boss et al. |
| 4,816,567 | A | 3/1989 | Cabilly et al. |
| 4,912,040 | A | 3/1990 | Kaufman et al. |
| 4,959,455 | A | 9/1990 | Clark et al. |
| 5,916,771 | A | 6/1999 | Hori et al. |
| 6,207,418 | B1 | 3/2001 | Hori et al. |
| 6,946,292 | B2 | 9/2005 | Kanda et al. |
| 2004/0058441 | A1 | 3/2004 | Pain et al. |
| 2007/0015239 | A1 | 1/2007 | Bihoreau et al. |
| 2008/0219969 | A1* | 9/2008 | Schmitthaeusler ........ 424/130.1 |
| 2009/0041780 | A1 | 2/2009 | Schmitthaeusler |
| 2009/0163699 | A1 | 6/2009 | Chamberlain |
| 2009/0203538 | A1 | 8/2009 | Sugioka et al. |

FOREIGN PATENT DOCUMENTS

| | | |
|---|---|---|
| FR | 2861080 A1 | 4/2005 |
| FR | 2899111 B1 | 10/2007 |
| WO | WO-8403564 A1 | 9/1984 |
| WO | WO-9309872 A1 | 5/1993 |
| WO | WO 94/09136 * | 4/1994 |
| WO | WO-99/54342 A1 | 10/1999 |
| WO | WO-03/011878 A2 | 2/2003 |
| WO | WO-03076601 A1 | 9/2003 |
| WO | WO-2005/044859 A2 | 5/2005 |
| WO | WO-2006051091 A1 | 5/2006 |
| WO | WO-2006113643 A3 | 9/2007 |
| WO | WO-2007118986 A2 | 10/2007 |
| WO | WO-2008026225 A3 | 9/2008 |
| WO | WO-2008142124 A1 | 11/2008 |
| WO | WO-2009031045 A3 | 4/2009 |
| WO | WO-2009124312 A3 | 1/2010 |
| WO | WO-2009048633 A3 | 7/2010 |
| WO | WO 2010/106180 | 9/2010 |

OTHER PUBLICATIONS

Vajdos et al., Comprehensive Functional Maps of the Antigen binding Site of an Anti-ErbB2 Antibody Obtained with Shotgun Scanning Mutagenesis, 2002, Journal of Molecular Biology, vol. 320, pp. 415-428.*

Bowie et al., Deciphering the Message in Protein Sequences: Tolerance to Amino Acid Substitutions, 1990, Science, vol. 247, No. 4948, pp. 1306-1310.*

Davies, Julian, et al., "Affinity Improvement of Single Antibody VH Domains: Residues in all Three Hypervariable Regions Affect Antigen Binding", Immunotechnology, vol. 2, (1996), pp. 169-179.

Edelman, R., et al., "Phase II Safety and Immunogenicity Study of Live Chikungunya Virus Vaccine TSI-GSD-218", Am. J. Trop. Med. Hyg., vol. 62, No. 6, (2000), pp. 681-685.

Garrone, Pierre, et al., "Generation and Characterization of a Human Monoclonal Autoantibody that Acts as a High Affinity Interleukin-1α Specific Inhibitor", Molecular Immunology, vol. 33, No. 7/8, (1996), pp. 649-658.

Grivard, P., et al., "Molecular and Serological Diagnosis of Chikungunya Virus Infection", Pathologie Biologie, vol. 55, (2007), pp. 490-494.

Grote, Monika, et al., "Human Monoclonal IgG Antibodies Derived from a Patient Allergic to Birch Pollen as Tools to Study the In Situ Localization of the Major Birch Pollen Allergen Bet v 1, by Immunogold Electron Microscopy", Journal of Allergy and Clinical Immunology, vol. 101., No. 1, (1998), pp. 60-66.

(Continued)

Primary Examiner — Benjamin P Blumel
(74) Attorney, Agent, or Firm — Polsinelli PC

(57) ABSTRACT

The invention relates to binding molecules against Chikungunya virus, which are able of neutralizing Chikungunya virus infectivity, and which can be used with therapeutic, diagnosis or research purposes, as well as to a pharmaceutical composition comprising said binding molecules.

13 Claims, 8 Drawing Sheets

(56) References Cited

OTHER PUBLICATIONS

Guillot-Chene, P., et al., "Towards an Industrial Control of the Cloning of Lymphcytes B Human for the Manufacturing of Monoclonal Antibodies Stemming from the Human Repertoire", Annales Pharmaceutiques Francaises, vol. 67, (2009), pp. 182-186.

Holt, Lucy J., et al., "Domain Antibodies: Proteins for Therapy", Trends in Biotechnology, vol. 21, No. 11, (2003), pp. 484-490.

Robin, Stephanie, et al., "Severe Bullous Skin Lesions Associated with Chikungunya Virus Infection in Small Infants", Eur. J. Pediatr., vol. 169, (2010), pp. 67-72.

Shukla, Jyoit, et al., "Development and Evaluation of Antigen Capture ELISA for Early Clinical Diagnosis of Chikungunya", Diagnostic Microbiology and Infectious Disease, vol. 65, (2009), pp. 142-149.

Traggiai, Elisabetta, et al., "An Efficient Method to Make Human Monoclonal Antibodies from Memory B Cells: Potent Neutralization of SARS Coronavirus", Nature Medicine, vol. 10, No. 8, (2004), pp. 871-875.

Bréhin, A., et al., "Production and characterization of mouse monoclonal antibodies reactive to Chikungunya envelope E2 glycoprotein", Virology, vol. 371, (2008), pp. 185-195.

Couderc, T., et al., "Prophylaxis and Therapy for Chikungunya Virus Infection", Journal of Infectious Diseases, vol. 200, (2009), pp. 516-523.

Gal-Tanamy, M., et al., "In vitro selection of a neutralization-resistant hepatitis C virus escape mutant", PNAS, vol. 105, No. 49, (2008), pp. 19450-19455.

Greiser-Wilke, I., et al., "Detection of Alphaviruses in a Genus-Specific Antigen Capture Enzyme Immunoassay Using Monoclonal Antibodies", Journal of Clinical Microbiology, vol. 29, No. 1, (1991), pp. 131-137.

Karpas, A., et al., "A human myeloma cell line suitable for the generation of human monoclonal antibodies", PNAS, vol. 98, No. 4, (2001), pp. 1799-1804.

Kwakkenbos, M., et al., "Generation of stable monoclonal antibody-producing BCR+ human memory B cells by genetic programming", Nat. Med., vol. 16, No. 1, (2010), pp. 123-128.

Laurent, P., et al., "Development of a Sensitive Real-Time Reverse Transciptase PCR Assay with an Internal Control to Detect and Quantify Chikungunya Virus", Chinical Chemistry, vol. 53, No. 8, (2007), pp. 1408-1414.

Lescar, J., et al., "Crystal Structure of a Cross-reaction Complex between Fab F9.13.7 and Guinea Fowl Lysozyme", Journal of Biological Chemistry, vol. 260, No. 30, (1995) pp. 18067-18076.

Michault, A., et al., "Chikungunya: First Steps toward Specific Treatment and Prophylaxis", Editorial Commentary, Journal of Infectious Diseases, vol. 200, (2009), pp. 489-491.

Morrison, S., et al., "Chimeric human antibody molecules: Mouse antigen-binding domains with human constant region domains", Proc. Natl. Acad. Sci. USA, vol. 81, (1984), pp. 6851-6855.

Mukhopadhyay, S., et al., "Mapping the Structure and Function of the E1 and E2 Glycoproteins in Alphaviruses", Structure, vol. 14, (2006), pp. 63-73.

Muthumani, K., et al., "Immunogenicity of Novel Consensus-Based DNA Vaccines Against Chikungunya Virus", Vaccine, vol. 26, No. 20, (2008), pp. 5128-5134.

Parida, M., et al., "Rapid and Real-Time Detection of Chikungunya Virus by Reverse Transcription Loop-Mediated Isothermal Amplification Assay", Journal of Clinichal Microbiology, vol. 45, No. 2, (2007), pp. 351-357.

Pletnev, S., et al., "Locations of Carbohydrate Sites on Alphavirus Glycoproteins Show that E1 Forms an Icosahedral Scaffold", Cell, vol. 105, (2001), pp. 127-136.

Shields, R., et al., "High Resolution Mapping of the Binding Site on Human IgGI for FcγRI, FcγRIII, FcγRIII, and FcRn and Design of IgG1 Variants with Improved Binding to the FcγR", The Journal of Biological Chemistry, vol. 276, No. 9, (2001), pp. 6591-6604.

Strauss, J., et al., "The Alphaviruses: Gene Expression, Replication, and Evolution", Microbiological Reviews, vol. 58, No. 3, (1994), pp. 491-562.

Tiller, T., et al., "Efficient generation of monoclonal antibodies from single human B cells by single cell RT-PCR and expression vector cloning", J. Immunol Methods, vol. 329, No. 1-2, (2008), pp. 112-124.

Wrammert, J., et al., "Rapid Cloning of High Affinity Human Monoclonal Antibodies Against Influenza Virus", Nature, vol. 453, No. 7195, (2008), pp. 667-671.

Sanz, L. et al., "Antibody Engineering: facing new challenges in cancer therapy", Acta Pharmacologica Sinica, vol. 26, No. 6, pp. 641-648, 2005.

Moore, G.L. et al., "Engineered Fc Variant antibodies with enhanced ability to recruit complement and mediate effector functions", mAbs, vol. 2, issue 2, pp. 181-189, Mar./Apr. 2010.

Lazar, G.A. et al., "Engineered antibody Fc variants with enhanced effector function", PNAS, vol. 103, No. 11, pp. 4005-4010, Mar. 14, 2006.

Kubota, T. et al., "Engineered therapeutic antibodies with improved effector functions", Cancer Science, vol. 100, No. 9, pp. 1566-1572, Sep. 2009.

Hinton, P.R. et al., "Engineered Human IgG Antibodies with Longer Serum Half-liveS in Primates", Journal of Biological Chemistry, vol. 279, No. 8, pp. 6213-6216, 2004.

Dall'Acqua, W.F. et al., "Properties of Human IgG1s Engineered for Enhanced Binding to the Neonatal Fc Receptor (FcRn)", Journal of Biological Chemistry, vol. 281, No. 33, pp. 23514-23524, Aug. 18, 2006.

\* cited by examiner

```
ATGGACATGAGGGTCCCCGCTCAGCTCCTGCTCTGGGCTCTGCTCCTCAGCTCCAGATGTGACATCCAGATGACCCAGTCTCCA        90
 M  D  M  R  V  P  A  Q  L  L  L  W  L  P  G  T  R  C  D  I  Q  M  T  Q  S  P

TCCTCCCTGTCTGCATCTGTAGGAGACAGAGTCACCATCACTTGCCGGGCGAGTCAGGGCATTAGCAATTCTTTAGCCTGGTATCAGCAG        180
 S  S  L  S  A  S  V  G  D  R  V  T  I  T  C  R  A  S  Q  G  I  S  N  S  L  A  W  Y  Q  Q
                                                    |_____CDR 1_____|

AAACCAGGGAAAGCCCCTAAGCTCCTGATCTATGCTGCATCCAGATTGGAAAGTGGGGTCCCATCAAGGTTCAGTGGCAGTGGATCTGGG        270
 K  P  G  K  A  P  K  L  L  I  Y  A  A  S  R  L  E  S  G  V  P  S  R  F  S  G  S  G  S  G
                              |_____CDR 2_____|

ACGGATTACACTCTCACCATCAGCAGCCTGCAGCCTGAAGATTTTGCAACTTATTACTGTCAACAGTATTATAGTACCCCGTACACTTTT        360
 T  D  Y  T  L  T  I  S  S  L  Q  P  E  D  F  A  T  Y  Y  C  Q  Q  Y  Y  S  T  P  Y  T  F
                                                       |_____CDR 3_____|

GGCCAGGGGACCAAGCTGGAGATCAAACGAACTGTGGCTGCACCATCTGTCTTCATCTTCCCGCCATCTGATGAGCAGTTGAAATCTGGA        450
 G  Q  G  T  K  L  E  I  K  R  T  V  A  A  P  S  V  F  I  F  P  P  S  D  E  Q  L  K  S  G

ACTGCCTCTGTTGTGTGCCTGCTGAATAACTTCTATCCCAGAGAGGCCAAAGTACAGTGGAAGGTGGATAACGCCCTCCAATCGGGTAAC        540
 T  A  S  V  V  C  L  L  N  N  F  Y  P  R  E  A  K  V  Q  W  K  V  D  N  A  L  Q  S  G  N

TCCCAGGAGAGTGTCACAGAGCAGGACAGCAAGGACAGCACCTACAGCCTCAGCAGCACCCTGACGCTGAGCAAAGCAGACTACGAGAAA        630
 S  Q  E  S  V  T  E  Q  D  S  K  D  S  T  Y  S  L  S  S  T  L  T  L  S  K  A  D  Y  E  K

CACAAAGTCTACGCCTGCGAAGTCACCCATCAGGGCCTGAGCTCGCCCGTCACAAAGAGCTTCAACAGGGGAGAGTGT
 H  K  V  Y  A  C  E  V  T  H  Q  G  L  S  S  P  V  T  K  S  F  N  R  G  E  C
```

Figure 2 (continued)

Chikungunya virus +
Irrelevant human IgG1

Chikungunya virus +
Anti-Chikungunya virus
human plasma

Chikungunya virus +
purified 5F10F175E2 (10µg/ml)

Chikungunya virus +
purified 8B10F8 (10µg/ml)

Chikungunya virus +
recombinant 5F10F175E2 (10µg/ml)

Chikungunya virus +
recombinant 8B10F8 (10µg/ml)

Figure 3

BINDING MOLECULES AGAINST CHIKUNGUNYA VIRUS AND USES THEREOF

RELATED APPLICATIONS

This application is a national stage application (under 35 U.S.C. §371) of PCT/EP2011/055402, filed Apr. 7, 2011, which claims priority of Singapore application 201002413-1, filed on Apr. 7, 2010, and European application 10305353.4, filed Apr. 7, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Rev_US_Seq_List. The size of the text file is 40 KB, and the text file was created on Mar. 21, 2013.

FIELD OF THE INVENTION

The present invention relates to binding molecules against Chikungunya virus. Particularly, said binding molecules are capable of neutralizing Chikungunya virus infectivity. Said binding molecules can be used with therapeutic, diagnosis or research purposes, among others. The invention also relates to a pharmaceutical composition comprising said binding molecules and more particularly, to the use thereof in the treatment or prevention of Chikungunya fever.

BACKGROUND OF THE INVENTION

Chikungunya fever is an emerging, epidemic disease, caused by an arbovirus and transmitted by the *Aedes* mosquitoes, of much significance for WHO's South-East Asia Region. The disease has been reported from countries of South and East Africa, South Asia and South-East Asia. In WHO's South-East Asia Region, outbreaks have been reported from India, Indonesia, Myanmar, Sri Lanka, Thailand and Maldives. Massive outbreaks of Chikungunya fever have occurred in recent years in India and in the island countries of the Indian Ocean. Similarly, Maldives reported outbreaks of Chikungunya fever for the first time in December 2006. Although not a killer disease, high morbidity rates and prolonged polyarthritis leading to considerable disability in a proportion of the affected population can cause substantial socio-economic impact in affected countries (WHO, guidelines for prevention&control of Chikungunya fever, 2009).

The Chikungunya virus (CHIKV) is a member of the genus *alphavirus* and family Togaviridae (reviewed by Strauss and Strauss, 1994, Microbiol Rev 58, 491-562). The alphaviruses are small enveloped single-stranded positive RNA viruses exhibiting a large cell tropism. The viral surfaces are covered in membrane-anchored spikes composed of triplets of heterodimers of the envelope E1 and E2 glycoproteins. The viral spike proteins facilitate attachment to cell surfaces and viral entry. The E1 envelope glycoprotein is a class II fusion protein that mediates low pH-triggered membrane fusion during virus infection. E2 is a 50 kDa type I transmembrane glycoprotein: the first 260 amino acids constitute the ectodomain, followed by about 100 amino acids that form the stem region, a spanning region of 30 amino acids, and a short cytoplasmic endodomain of 30 amino acids (Plenetv, et al., 2001, Cell 105, 127-136; Mukhopadhyay, et al., 2006, Structure 14, 63-73). pE2 (the 62-kDa precursor to the E3 and E2 proteins) and E1 are assembled as heterodimers in the endoplasmic reticulum (Strauss and Strauss, 1994, Microbiol Rev 58, 491-562). After the cleavage of pE2 in the Golgi apparatus to form E3 and E2, the E1-E2 complexes are transported to the plasma membrane (PM). The interaction of the cytoplasmic E2 endodomain with the preassembled nucleocaspid is one of the initial steps in the process of virus envelopment at the PM. Integrity of virion is maintained by direct interactions between E1 and E2 (Strauss and Strauss, 1994, Microbiol Rev 58, 491-562). During the course of *alphavirus* life cycle, the E2 glycoprotein is responsible for receptor binding. In general, neutralizing antibodies against alphaviruses recognize epitopes in E2 rather than E1 (Roehrig, J. T. 1986. The use of monoclonal antibodies in studies of the structural proteins of togaviruses and flaviviruses, p. 251-278. In S. Schlesinger and M. J. Schlesinger (ed.), The Togaviridae and Flaviviridae. Plenum Publishing Corp., New York).

Biological diagnosis of CHIK virus infection is essentially based on quantitative real-time RT-PCR-based method during the initial viraemic phase (Edwards et al., 2007, J. Clin. Virol. 39, 271-275; Laurent et al., 2007, Clin. Chem. 53, 1408-1414; Parida et al., 2007, J. Clin. Microbiol. 45, 351-357). Serological methods detect anti-CHIK IgM early times after the first clinical manifestations and specific IgG after two weeks (Pialoux et al., 2007, Lancet Infect. Dis. 7, 319-327). However, ELISA and immunodetection assays are poorly specific and sensitive due the cross reactivity of Chikungunya virus with related members of the Semliki Forest (SF) antigenic complex (Greiser-Wilke et al., 1991, J. Clin. Microbiol. 29, 131-137).

More recently, Brehin and colleagues (Brehin et al., 2008, Virology 371, 185-195) have developed some monoclonal antibodies (mAbs) reactive to CHIKV E2 glycoprotein for diagnosis and research purposes, which were also described in WO 2009/031045. The three anti-CHIKV-E2 mAbs showed cross-reactivity with the O'nyong-nyong viral strains Igbo-Ora and ONN-59. CHIKV, Igbo-Ora and ONN-59 are serologically classified in the SF antigenic complex (Strauss and Strauss, 1994, Microbiol Rev 58, 491-562). These monoclonal antibodies are of murine origin, and although they have demonstrated significant reactivity with CHIKV-associates E2 glycoprotein they failed to neutralize CHIKV infection of primate cells in vitro. Besides, a first commercial Chikungunya virus indirect immunofluorescence test (IIFT) is commercialized by Euroimmun AG, Germany for analyzing the CHIKV specific immune response. This test was evaluated by Litzba et al. (Litzba et al., 2008, Journal of virological methods, 149(1), 175-179).

In the recent years, there has been an explosive re-emergence of Chikungunya fever. Thus, although some advances have been undertaken to provide a reliable test allowing the detection and monitoring of CHIKV specific antibodies, there is still a need to develop new anti-CHIKV monoclonal antibodies for diagnosis and research purposes on Chikungunya virus infection.

On the other hand, a specific treatment is not available and there is no approved vaccine for the prevention of Chikungunya fever. Currently, vector control is the only way to prevent and control the outbreaks. Vector control is not an easy task and insecticide spraying is not always effective and desirable (WHO, guidelines for prevention&control of Chikungunya fever, 2009).

Symptomatic treatment is recommended after excluding more serious conditions. Symptomatic or supportive treatment basically comprises rest and use of acetaminophen or paracetamol to relieve fever and ibuprofen, naproxen or other non-steroidal anti-inflammatory agent (NSAID) to relieve the arthritic component. Patients with persistent or chronic phase of arthritis who fail to respond to NSAID may show some response to chloroquine phosphate. The latter may act as a weak broad spectrum antiviral agent apart from being an anti-inflammatory agent. Use of corticosteroids in managing Chikungunya related arthropathy has in general been a contentious issue and has to be the last resort in a clinical decision (WHO, guidelines for prevention&control of Chikungunya fever, 2009).

While there has been extensive work in vaccinology for several other alphaviruses (Rayner et al., 2002, Rev Med Virol 12, 279-296; Nalca et al., 2003, Antiviral Res 60, 153-174); Johnston & Davis, 2004, Arch Virol Suppl 18, 207-220), the history of vaccine development for CHIKV is short and none of these efforts have yet resulted in a licensed vaccine. Recently, a Phase II study was performed with a serially passaged live chikungunya virus (Edelman et al., 2000, Am J Trop Med Hyg. 62(6), 681-5) with good immunogenicity and tolerance results. However, this vaccine seems not to have reached market authorization and further efforts are being made to find a Chikungunya vaccine, see for example the in vivo study on the immunogenicity of consensus-based DNA vaccines against CHIKV performed by Muthumani et al. (Muthumani K. et al., 2008, Vaccine 26(40), 5128-34).

With regards to the immunotherapy strategies against Chikungunya virus infection, the use of a concentrate of human immunoglobulins (IgA, IgM and IgG) has been previously described, as well as F(ab)'2 and/or Fab fragments specific to an arbovirus (i.e. Chikungunya virus) for use as a medicament in the treatment of arbovirosis, see WO 2007/118986.

Furthermore, studies with neutralizing mAbs have been reported for several alphaviruses including Sindbis virus (SIN), Venezuelan equine encephalitis virus (VEE), Ross River virus (RR), Semliki Forest virus (SF), Eastern equine encephalitis virus (EEE) and Western equine encephalitis virus (WEE) (see, e.g. Roehrig, J. T. 1986. The use of monoclonal antibodies in studies of the structural proteins of togaviruses and flaviviruses, p. 251-278. In S. Schlesinger and M. J. Schlesinger (ed.), The Togaviridae and Flaviviridae. Plenum Publishing Corp., New York). Recently, human polyvalent immunoglobulins were purified from plasma samples obtained from donors in the convalescent phase of CHIKV infection, and the preventive and curative effects of these immunoglobulins were investigated (Couderc et al., 2009, J Infect Dis. 2009, 200(4), 489-91). However, to our knowledge, at present no neutralizing monoclonal antibodies against Chikungunya virus have been described, let alone fully human neutralizing antibodies.

Since at present there is no vaccine or specific treatment available on the market to combat the Chikungunya fever, several efforts are being undertaken to obtain a safe and active therapy to be administered to patients suffering from Chikungunya fever and also to obtain a protective therapy against the virus infection. Accordingly, there is a need for providing therapies that are useful in the prevention and/or treatment of the Chikungunya fever.

SUMMARY OF THE INVENTION

The invention provides new binding molecules against Chikungunya virus (CHIKV). In particular, two monoclonal antibodies specifically binding to an epitope located in an antigenic site of one of the Chikungunya virus envelope proteins are provided. Furthermore, these antibodies are fully human antibodies with CHIKV neutralizing properties which make them particularly useful for the treatment or prevention of Chikungunya fever, thus avoiding all the secondary effects or unwanted reactions associated to murine, chimeric or humanized antibodies in the treatment of human patients.

In accordance with a first aspect of this invention, we provide an isolated binding protein that specifically binds to Chikungunya virus, comprising a heavy chain amino acid sequence comprising at least one of the CDR's selected from the group consisting of: (a) CDRH1's of SEQ ID NOs: 10 or 30, (b) CDRH2's of SEQ ID NOs: 12 or 32, and (c) CDRH3's of SEQ ID NOs: 14 or 34, and/or a light chain amino acid sequence comprising at least one of the CDR's selected from the group consisting of: (d) CDRL1's of SEQ ID NOs: 16 or 36, (e) CDRL2's of SEQ ID NOs: 18 or 38, and (f) CDRL3's of SEQ ID NOs: 20 or 40.

A second aspect of the present invention relates to a functional variant of a binding protein of the invention characterized in that said functional variant binds to Chikungunya virus.

A third aspect of the present invention refers to an immunoconjugate of a binding protein or a functional variant of the invention wherein said binding protein or functional variant is coupled to at least one labeling and/or effector group.

A further aspect of the present invention relates to an isolated nucleic acid molecule comprising a nucleic acid sequence encoding a binding protein, a functional variant or an immunoconjugate of the invention.

Another aspect of the present invention pertains to a vector comprising a nucleic acid molecule of the invention. A further aspect of the invention relates to a host cell comprising the nucleic acid molecule or the vector of the invention.

In accordance to an additional aspect of this invention, we provide a method for producing a binding protein, a functional variant or an immunoconjugate of the invention, comprising the step of producing said binding protein, functional variant or immunoconjugate in a host cell of the invention and optionally, isolating said binding protein, functional variant or immunoconjugate.

In yet another aspect of the present invention, we provide a pharmaceutical composition comprising as an active agent at least one isolated binding protein, at least one functional variant or at least one immunoconjugate of the invention; and a pharmaceutically acceptable carrier, diluent or adjuvant.

A related aspect of the present invention refers to an isolated binding protein, a functional variant or an immunoconjugate of the invention for use as a medicament. Moreover, the present invention relates in a further aspect to a isolated binding protein, a functional variant, an immunoconjugate and/or the pharmaceutical composition of the invention for use in the prevention or treatment of the infection of an arbovirus from the Togaviridae family, preferably from the genus *alphavirus* more preferably the Chikungunya virus.

In even another aspect, the present invention relates to the use of a binding protein, a functional variant or an immunoconjugate of the invention for diagnostic or screening purposes.

A further aspect of the present invention relates to a kit comprising at least one isolated binding protein, at least one functional variant, at least one immunoconjugate and/or at least one pharmaceutical composition of the invention.

BRIEF DESCRIPTION OF THE FIGURES

Figure 1:
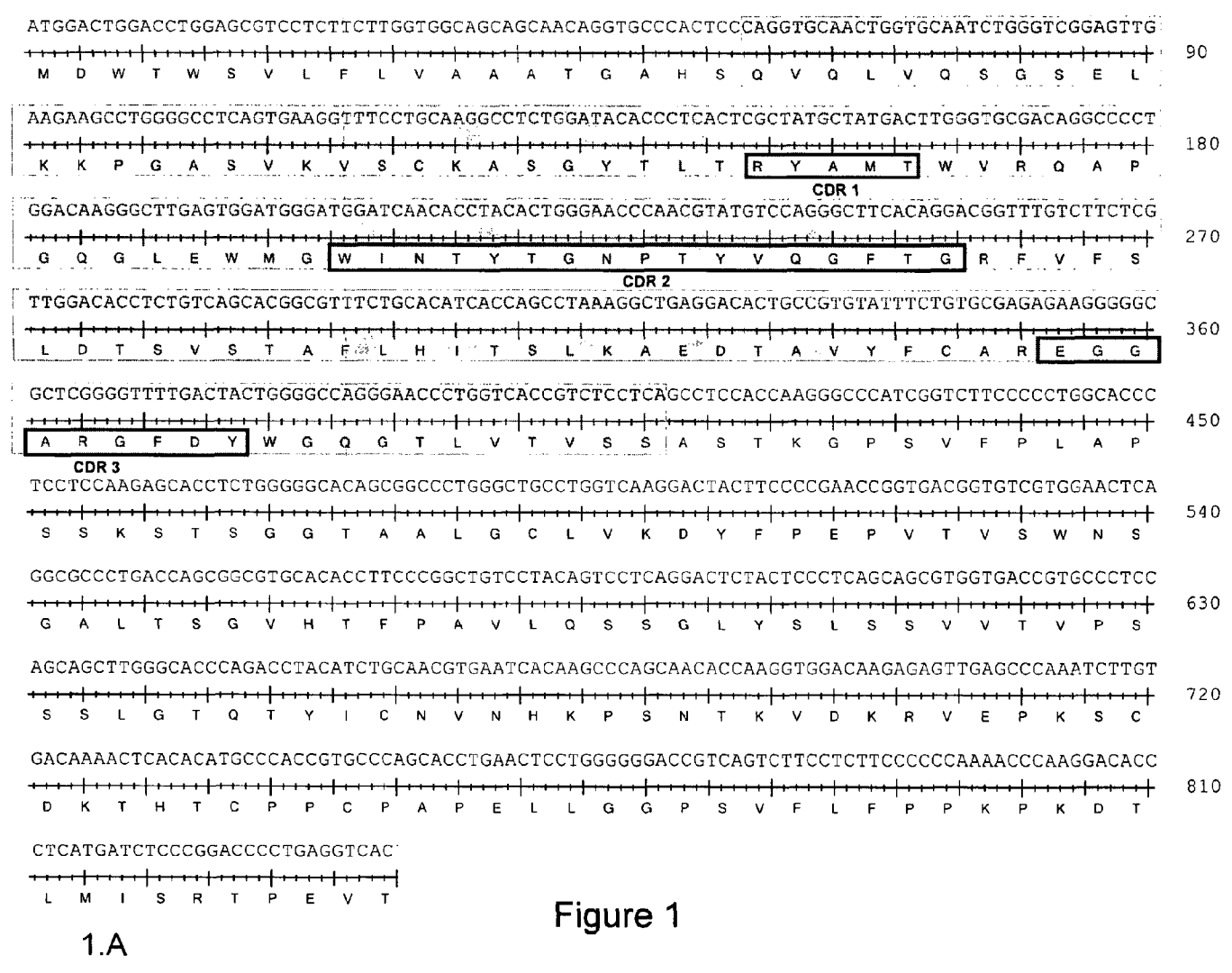
Figure 1:
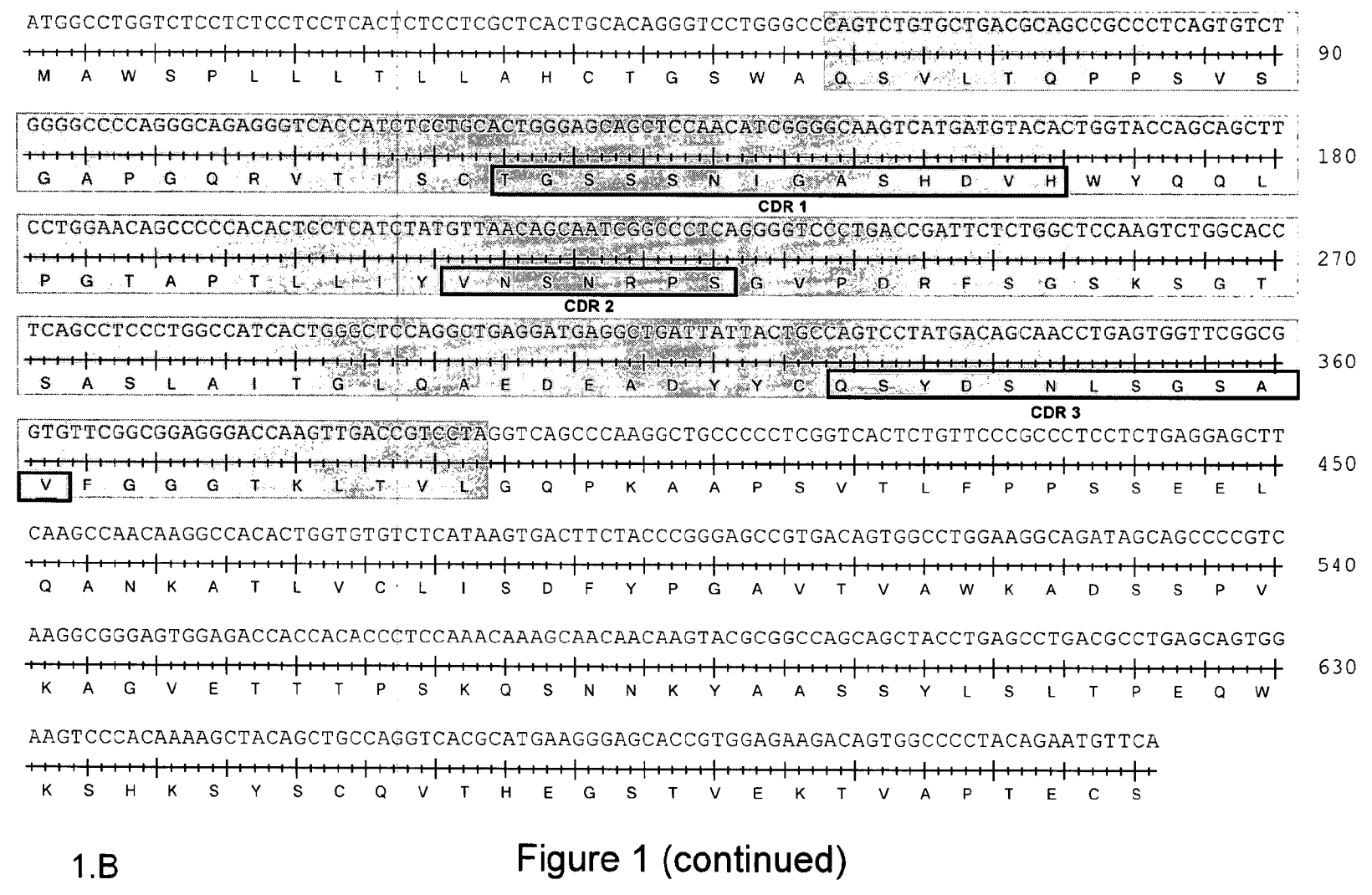

FIG. 1A shows the nucleotide (SEQ ID No. 1) and corresponding amino acid (SEQ ID No. 50) sequences of the heavy chain variable domain (VH) and a partial region of the Constant Heavy 1 (CH1) domain of the 5F10F175E2 antibody and FIG. 1B shows the nucleotide (SEQ ID No. 3) and corresponding amino acid (SEQ ID No. 51) sequences of whole light chain of the 5F10F175E2 antibody. Leader sequences are indicated in light grey. Variable domains (VH and VL, respectively) are highlighted in dark grey. The Complementary Determining Regions (CDR's) are also indicated for each of the variable domains.

FIG. 2A shows the nucleotide (SEQ ID No. 21) and corresponding amino acid (SEQ ID No. 52) sequences of the heavy chain variable domain (VH) and a partial region of the Constant Heavy 1 (CH1) domain of the 8B10F8 antibody and FIG. 2B shows the nucleotide (SEQ ID No. 23) and corresponding amino acid (SEQ ID No. 53) sequences of whole light chain of the 8B10F8 antibody. The leader sequence (5' Untranslated region; 5'UTR) is indicated in light grey. Variable domains (VH and VL, respectively) are highlighted in dark grey. The Complementary Determining Regions (CDR's) are also indicated for each of the variable domains.

FIG. 3 shows the results of the indirect immunofluorescence assay performed to assess the infection of HEK 293T cells by Chikungunya virus, confirming the in vitro neutralizing properties of the recombinant antibodies (rec8B10F8 and rec5F10F175E2) and of the isolated antibodies (8B10F8 and 5F10F175E2) against the Chikungunya virus A226 and A226V strains. Images were obtained using a fluorescent microscope (×10 magnificence, NIKON ECLIPSE TS 100).

DETAILED DESCRIPTION

Binding Proteins

Figure 4:
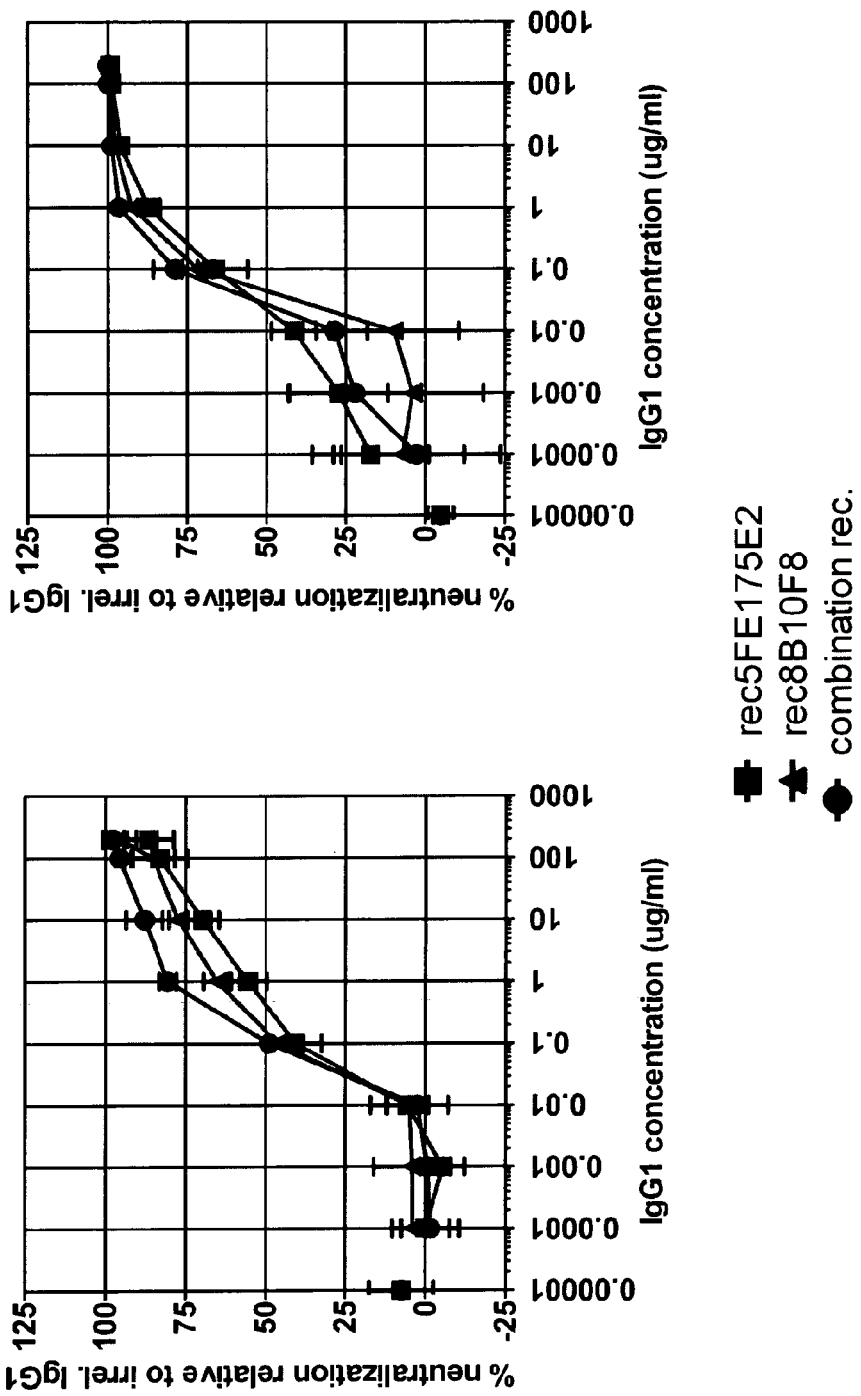
FIG. 4 shows the dose-response neutralization curves of the recombinant mAbs (rec8B10F8 and rec5F10F175E2) against Chikungunya virus A226 and A226V strains, as neutralization percentage (%) relative to an irrelevant IgG1. rec5F10F175E2 antibody is represented as a square (-■-), rec8B10F8 antibody is represented as a triangle (-▲-) and both antibodies used in combination as a dot (-●-).

In a first aspect, the present invention encompasses binding proteins capable of specifically binding to Chikungunya virus (CHIKV).

The term "specifically binding", as used herein, in reference to the interaction of a binding protein, e.g. an antibody, and its binding partner, e.g. an antigen, means that the interaction is dependent upon the presence of a particular structure, e.g. an antigenic determinant or epitope, on the binding partner. In other words, the antibody preferentially binds or recognizes the binding partner even when the binding partner is present in a mixture of other molecules or organisms. The binding may be mediated by covalent or noncovalent interactions or a combination of both. In yet other words, the term "specifically binding" means immunospecifically binding to an antigen or a fragment thereof and not immunospecifically binding to other antigens. A binding protein that immunospecifically binds to an antigen may bind to other peptides or polypeptides with lower affinity as determined by, e.g., radioimmunoassays (RIA), enzyme-linked immunosorbent assays (ELISA), BIACORE, or other assays known in the art. Binding proteins or fragments thereof that immunospecifically bind to an antigen may be cross-reactive with related antigens. Preferably, binding proteins or fragments thereof that immunospecifically bind to an antigen do not cross-react with other antigens.

Chikungunya virus is part of the genus *alphavirus*. According to Strauss and Strauss (Strauss and Strauss, 1994, Microbiol Rev 58, 491-562), in total, the genus *alphavirus* have 26 recognized members (i.e. genotypes). Alphaviruses have been classified in 4 main groups according to its serological cross-reaction, i.e., the Venezuelan equine encephalitis (VEE/EEE) group, the Semliki Forest (SF) group, the Sindbis virus (SIN) group and the Western Equine Encephalitis (WEE) group. Table I below lists some of the currently recognized alphaviruses, together with their geographical distribution and their serological group. Besides binding to Chikungunya virus, the binding proteins of the invention may also be capable of binding to other genotypes of the genus *alphavirus*, including but not limited to those listed in Table I.

TABLE I

| Group | Virus | Geographic distribution |
|---|---|---|
| VEE/EEE | Eastern equine encephalitis (EEE) | America |
| | Venezuelan equine encephalitis (VEE) | America |
| | Everglades | America |
| | Mucambo | America |
| | Pixuna | America |
| SF | Semliki Forest (SF) | Africa, Eurasia |
| | Middelburg | Africa |
| | Chikungunya | Africa, Asia |
| | O'Nyong Nyong | Africa |
| | Ross River | Australia |
| | Barma Forest | Australia |
| | Getah | Australia, Asia |
| | Sagiyama | Japan |
| | Bebaru | Malaysia |
| | Mayaro | South America |
| | Una | South America |
| | Ndumu | Africa |
| SIN | Sindbis (SIN) | Africa, Asia, Europe, Australia, Scandinavia |
| | Aura | America |
| | Whataroa | New Zeeland |
| | Babanki | Africa |
| | Kyzylagash | Russia |
| WEE | Western equine encephalitis | America |

Furthermore, the binding proteins of the invention may even be capable of binding to viruses other than alphaviruses of the Togaviridae family, such as those belonging to the genus *rubivirus* or others. Further information on the Togaviridae family and its taxonomic structure and members can be found on the Index of Viruses—Togaviridae (2006). In: ICTVdB—The Universal Virus Database, version 4. Birchen-Osmond, C (Ed), Columbia University, New York, USA.

The binding proteins of the invention may be capable of specifically binding to Chikungunya virus in its natural form or in its inactivated/attenuated form. General viral inactivation methods well known to the skilled artisan such as inter alia pasteurization (wet heat), dry heat treatment, vapor heat treatment, treatment with low pH, treatment with organic solvent/detergent, nanofiltration and/or UV light irradiation may be used. Preferably, the inactivation is performed by heat-treatment for 1 hour at 56° C.

The binding proteins of the invention may also be capable of specifically binding to one or more fragments of the Chikungunya virus such as inter alia a preparation of one or more proteins and/or (poly) peptides derived from Chikungunya virus or a cell transfected with a Chikungunya virus protein and/or (poly) peptide. For methods of treatment and/or prevention of Chikungunya virus the binding proteins of the invention are preferably capable of specifically binding to surface accessible proteins of Chikungunya virus such as the E1 or E2 glycoproteins (Strauss and Strauss, 1994, Microbiol Rev 58, 491-562). For diagnostic purposes the binding proteins of the invention may also be capable of specifically binding to proteins not present on the surface of Chikungunya virus. The amino acid sequence of surface accessible and internal proteins of various known strains of Chikungunya virus can be found in the EMBL-database and/or other databases.

Preferably, the fragment at least comprises an antigenic determinant recognized by the binding proteins of the invention. An "antigenic determinant" as used herein is a moiety, such as a Chikungunya virus (poly) peptide, (glyco)protein, or analog or fragment thereof, that is capable of binding to a binding proteins of the invention with sufficiently high affinity to form a detectable antigen-binding protein complex.

Typically, binding proteins according to the invention can bind to their binding partners, i.e. Chikungunya virus or fragments thereof such as Chikungunya virus proteins, with an affinity constant (Kd-value) that is lower than $0.2 \times 10^{-4}$ M, $1.0 \times 10^{-5}$ M, $1.0 \times 10^{-6}$ M, $1.0 \times 10^{-7}$ M, preferably lower than $1.0 \times 10^{-8}$ M, more preferably lower than $1.0 \times 10^{-9}$ M, more preferably lower than $1.0 \times 10^{-10}$ M, even more preferably lower than $1.0 \times 10^{-11}$ M, and in particular lower than $1.0 \times 10^{-12}$ M. The affinity constants can vary for different antibody isotypes. Affinity constants can for instance be measured using surface plasmon resonance, i.e. an optical phenomenon that allows for the analysis of real-time biospecific interactions by detection of alterations in protein concentrations within a biosensor matrix, in particular using the BIACORE system (GE Healthcare).

The binding proteins according to the invention may bind to Chikungunya virus in purified/isolated or non-purified/non-isolated form. The binding proteins may bind to Chikungunya virus in soluble form such as for instance in a sample or may bind to Chikungunya virus bound or attached to a carrier or substrate, e.g., microtiter plates, membranes and beads, etc. Carriers or substrates may be made of glass, plastic (e.g., polystyrene), polysaccharides, nylon, nitrocellulose, or teflon, etc. The surface of such supports may be solid or porous and of any convenient shape. Alternatively, the binding proteins may also bind to fragments of Chikungunya virus such as proteins or (poly) peptides of the Chikungunya virus. In an embodiment the binding proteins are capable of specifically binding to the Chikungunya virus E2 or E1 protein or to a fragment thereof. The Chikungunya virus proteins or (poly) peptides may either be in soluble form or may bind to Chikungunya virus bound or attached to a carrier or substrate as described above. In another embodiment cells transfected with Chikungunya virus proteins or (poly) peptides may be used as binding partner for the binding proteins.

In one embodiment of the present invention, the isolated binding protein of the invention comprises a heavy chain amino acid sequence comprising at least one of the CDR's selected from the group consisting of: (a) CDRH1's of SEQ ID NOs: 10 or 30, (b) CDRH2's of SEQ ID NOs: 12 or 32, and (c) CDRH3's of SEQ ID NOs: 14 or 34, and/or a light chain amino acid sequence comprising at least one of the CDR's selected from the group consisting of: (d) CDRL1's of SEQ ID NOs: 16 or 36, (e) CDRL2's of SEQ ID NOs: 18 or 38, and (f) CDRL3's of SEQ ID NOs: 20 or 40. Preferably, the isolated binding protein comprises both the heavy chain amino acid sequence and the light chain amino acid sequence.

The term "complementarity determining regions" (CDR) as used herein means sequences within the variable regions of binding proteins, such as immunoglobulins, that usually contribute to a large extent to the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

The CDR3 region of the variable domain of the heavy chain (CDRH3) provides typically with the greatest source of molecular diversity within the antibody binding-site (Xu et al., 2000, Immunity, 13(1):37-45). Accordingly, preferably, the isolated binding protein of the invention comprises a heavy chain amino acid sequence comprising at least one of the CDR's selected from SEQ ID NO: 14 and SEQ ID NO: 34.

In another embodiment of the present invention, the isolated binding protein of the invention comprises a heavy chain amino acid sequence that comprises a CDRH1 selected from SEQ ID NOs: 10 or 30, a CDRH2 selected from SEQ ID NOs: 12 or 32, and a CDRH3 selected from SEQ ID NOs: 14 or 34, and/or a light chain amino acid sequence that comprises a CDRL1 selected from SEQ ID NOs: 16 or 36, a CDRL2 selected from SEQ ID NOs: 18 or 38, and a CDRL3 selected from SEQ ID NOs: 20 or 40. Preferably, said isolated binding protein comprises both the heavy chain amino acid sequence and the light chain amino acid sequence.

In a further embodiment, the isolated binding protein of the invention comprises a heavy chain amino acid sequence that comprises the CDRH1 of SEQ ID NO: 10, the CDRH2 of SEQ ID NO: 12, and the CDRH3 of SEQ ID NO: 14, and/or a light chain amino acid sequence that comprises the CDRL1 of SEQ ID NO: 16, the CDRL2 of SEQ ID NO: 18, and the CDRL3 of SEQ ID NO: 20.

In yet another embodiment, the isolated binding protein of the invention comprises a heavy chain amino acid sequence that comprises the CDRH1 of SEQ ID NO: 30, the CDRH2 of SEQ ID NO: 32, and the CDRH3 of SEQ ID NO: 34, and/or a light chain amino acid sequence that comprises the CDRL1 of SEQ ID NO: 36, the CDRL2 of SEQ ID NO: 38, and the CDRL3 of SEQ ID NO: 40.

In another embodiment, the isolated binding protein of the invention comprises a heavy chain amino acid sequence which comprises a VH domain amino acid sequence selected from the group consisting of SEQ ID Nos: 6 or 26, and/or a light chain amino acid sequence that comprises a VL domain amino acid sequence selected from the group consisting of SEQ ID NOs: 8 or 28. In a preferred embodiment, the isolated binding protein of the invention comprise the VH domain amino acid sequence of SEQ ID NO: 6 and the VL domain amino acid sequence of SEQ ID NO: 8. Alternatively, the isolated binding protein of the invention comprises the VH domain amino acid sequence of SEQ ID NO: 26 and the VL domain amino acid sequence of SEQ ID NO: 28.

In further embodiment, the isolated binding protein of the invention comprises a heavy chain amino acid sequence which comprises the amino acid sequence of SEQ ID NO: 2 or SEQ ID NO: 22 and/or a light chain amino acid sequence that comprises the amino acid sequence of SEQ ID NO: 4 or SEQ ID NO: 24. In a preferred embodiment, the isolated binding protein of the invention comprises a heavy chain amino acid sequence which comprises the amino acid sequence of SEQ ID NO: 2 and a light chain amino acid sequence which comprises the amino acid sequence of SEQ ID NO: 4. Alternatively, the isolated binding protein of the invention comprises a heavy chain amino acid sequence which comprises the amino acid sequence of SEQ ID NO: 22 and a light chain amino acid sequence which comprises the amino acid sequence of SEQ ID NO: 24.

In a particular embodiment, the binding protein of the invention is a scaffold protein having an antibody like binding activity or an antibody, i.e. an anti-CHIKV antibody.

Within the context of the present invention, the term "scaffold protein", as used herein, means a polypeptide or protein with exposed surface areas in which amino acid insertions, substitutions or deletions are highly tolerable. Examples of scaffold proteins that can be used in accordance with the present invention are protein A from *Staphylococcus aureus*, the bilin binding protein from *Pieris brassicae* or other lipocalins, ankyrin repeat proteins, and human fibronectin (reviewed in Binz and Plückthun, 2005, Curr Opin Biotechnol 16, 459-69 and in Plückthun, A., 2009, Recombinant Antibodies for Immunotherapy: Alternative Scaffolds: Expanding the Options of Antibodies (Little, M., ed), pp. 243-271, Cambridge University Press, New York). Engineering of a scaffold protein can be regarded as grafting or integrating an affinity function onto or into the structural framework of a stably folded protein. Affinity function means a protein binding affinity according to the present invention. A scaffold can be structurally separable from the amino acid sequences conferring binding specificity. A scaffold protein having an antibody like binding activity can for instance be derived from an acceptor polypeptide containing the scaffold domain, which can be grafted with binding domains of a donor polypeptide to confer the binding specificity of the donor polypeptide onto the scaffold domain containing the acceptor polypeptide. Said inserted binding domains may be, for example, the complementarity determining region (CDR) of an antibody, in particular an anti-CHIKV antibody. In one embodiment of the present invention, at least one of said inserted binding domains is one of the CDRs of the antibodies identified in the Examples (i.e. 8B10F8, 5F10F175E2, rec8B10F8 and rec5F10F175E2 antibodies), as above described. Insertion can be accomplished by various methods known to those skilled in the art including, for example, polypeptide synthesis, nucleic acid synthesis of an encoding amino acid as well by various forms of recombinant methods well known to those skilled in the art.

In a preferred embodiment, the binding protein of the invention is an antibody. The term "antibody" or "anti-CHIKV antibody", as used herein, means a monoclonal antibody, a polyclonal antibody, a recombinant antibody, a humanized antibody (Jones et al., 1986, Nature 321, 522-525; Riechmann et al., 1988, Nature 332, 323-329; and Presta, 1992, Curr. Op. Struct. Biol. 2, 593-596), a chimeric antibody (Morrison et al., 1984, Proc. Natl. Acad. Sci. U.S.A. 81, 6851-6855), a multispecific antibody (e.g. a bispecific antibody) formed from at least two antibodies, or an antibody fragment thereof. The term "antibody fragment" comprises any portion of the afore-mentioned antibodies, preferably their antigen binding or variable regions. Examples of antibody fragments include Fab fragments, Fab' fragments, F(ab')$_2$ fragments, Fv fragments, diabodies (Hollinger et al., 1993, Proc. Natl. Acad. Sci. U.S.A. 90, 6444-6448), single chain antibody molecules (Plückthun, A., 1994, in The pharmacology of monoclonal antibodies: Antibodies from *Escherichia coli* (Rosenberg, M., and Moore, G. P., eds), Vol. 113, pp. 269-315, Springer Verlag, Berlin) and other fragments as long as they exhibit the desired capability of binding to Chikungunya virus.

In addition, the term "antibody" or "anti-CHIKV antibody", as used herein, may include antibody-like molecules that contain engineered sub-domains of antibodies or naturally occurring antibody variants. These antibody-like molecules may be single-domain antibodies such as VH-only or VL-only domains derived either from natural sources such as camelids (Muyldermans et al., 2001, J Biotechnol. 74(4), 277-302) or through in vitro display of libraries from humans, camelids or other species (Holt et al., 2003, Trends Biotechnol. 21, 484-90).

In another preferred embodiment the binding protein of the invention is an antibody fragment.

In accordance with the present invention, the "Fv fragment" is the minimum antibody fragment that contains a complete antigen-recognition and -binding site. This region consists of a dimer of one heavy- and one light-chain variable domain in tight, non-covalent association. It is in this configuration that the three CDR's of each variable domain interact to define an antigen-binding site on the surface of the VH-VL dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site. Derivatives of Fv fragments, such as scFv (single-chain Fv) and dsFv (disulfide-stabilized Fv), which have been modified to increase stability of the recombinant Fv fragment are also included. The "Fab fragment" also contains the constant domain of the light chain and the first constant domain (CH1) of the heavy chain. The "Fab fragment" differs from the "Fab' fragment" by the addition of a few residues at the carboxy terminus of the heavy chain CH1 domain including one or more cysteines from the antibody hinge region. The "F(ab')$_2$ fragment" originally is produced as a pair of "Fab' fragments" which have hinge cysteines between them. Methods of preparing such antibody fragments, such as papain or pepsin digestion, are known to those skilled in the art.

In a further preferred embodiment of the present invention, the anti-CHIKV antibody of the invention is of the IgA-, IgD-, IgE-, IgG- or IgM-type, preferably of the IgG- or IgM-type including, but not limited to, the IgG1-, IgG2-, IgG3-, IgG4-, IgM1- and IgM2-type. In most preferred embodiments, the antibody is of the IgG1-, IgG2- or IgG4-type. More preferably, of the IgG1-type.

In certain respects, e.g. in connection with the generation of antibodies as therapeutic candidates against Chikungunya virus, it may be desirable that the anti-CHIKV antibody of the invention is capable of fixing complement and participating in complement-dependent cytotoxicity (CDC). There are a number of isotypes of antibodies that are capable of the same including without limitations the following: murine IgM, murine IgG2a, murine IgG2b, murine IgG3, human IgM, human IgG1, human IgG3, and human IgA. It will be appreciated that antibodies that are generated need not initially possess such an isotype but, rather the antibody as generated can possess any isotype and the antibody can be isotype switched by appending the molecularly cloned V region genes or cDNA to molecularly cloned constant region genes or cDNAs in appropriate expression vectors using conventional molecular biology techniques that are well known in the art and then expressing the antibodies in host cells using techniques known in the art. The isotype-switched antibody may also possess an Fc region that has been molecularly engineered to possess superior CDC over naturally occurring variants (Idusogie et al., 2001, J Immunol. 166, 2571-2575) and expressed recombinantly in host cells using techniques known in the art. Such techniques include the use of direct recombinant techniques (see e.g. U.S. Pat. No. 4,816,397), cell-cell fusion techniques (see e.g. U.S. Pat. No. 5,916,771 and U.S. Pat. No. 6,207,418), among others. In the cell-cell fusion technique, a myeloma or other cell line such as CHO is prepared that possesses a heavy chain with any desired isotype and another myeloma or other cell line such as CHO is prepared that possesses the light chain. Such cells can, thereafter, be fused and a cell line expressing an intact antibody can be isolated. By way of example, a human anti-CHIKV IgG4 antibody, that possesses the desired binding to the Chikungunya virus antigen, could be readily isotype switched to generate a human IgM, human IgG1 or human IgG3 isotype, while still possessing the same variable region. Such molecule might then be capable of fixing complement and participating in CDC.

Moreover, it may also be desirable for the anti-CHIKV antibody of the invention to be capable of binding to Fc receptors on effector cells, such as monocytes and natural killer (NK) cells, and participate in antibody-dependent cellular cytotoxicity (ADCC). There are a number of isotypes of antibodies that are capable of the same, including without limitations the following: murine IgG2a, murine IgG2b, murine IgG3, human IgG1 and human IgG3. It will be appreciated that antibodies that are generated need not initially possess such an isotype but, rather the antibody as generated can possess any isotype and the antibody can be isotype switched by appending the molecularly cloned V region genes or cDNA to molecularly cloned constant region genes or cDNAs in appropriate expression vectors using conventional molecular biological techniques that are well known in the art and then expressing the antibodies in host cells using techniques known in the art. The isotype-switched antibody may also comprise an Fc region that has been molecularly engineered to possess superior ADCC over naturally occurring variants (Shields et al., 2001, J Biol Chem. 276, 6591-6604) and expressed recombinantly in host cells using techniques known in the art. Such techniques include the use of direct recombinant techniques (see e.g. U.S. Pat. No. 4,816,397), cell-cell fusion techniques (see e.g. U.S. Pat. No. 5,916,771 and U.S. Pat. No. 6,207,418), among others. Such molecule might then be capable of binding to FcγR on effectors cells and participating in ADCC.

Antibodies with superior ADCC activity may be obtained by modifying the oligosaccharides profile of IgG's, by using different strategies such as for example, glycosylation inhibition, genetic modifications, amino acid changes in FcR, transgenesis or production in cell lines producing naturally unfucosilated antibodies. Examples of particular genetic engineering strategies are those used by companies such as GLYCART, KYOWA or LFB. GLYCART BIOTECHNOLOGY AG (Zurich, CH) has expressed N-acetyl-glucosaminyltransferase III (GnTIII) which catalyzes the addition of the bisecting GlcNac residue to the N-linked oligosaccharide, in a CHO cell line, and showed a greater ADCC of the IgG1 antibody produced (WO 99/54342; WO 03/011878; WO 2005/044859). On the other hand, by removing or supplanting fucose from the Fc portion of the antibody, KYOWA HAKKO KOGYO (Tokyo, Japan) has enhanced Fc binding and improved ADCC, and thus the efficacy of the Mab (U.S. Pat. No. 6,946,292). More recently, Laboratoire Francais du Fractionnement et des Biotechnologies (LFB) (France) showed that the ratio Fuc/Gal in Mab oligosaccharide should be equal or lower than 0.6 to get antibodies with a high ADCC (FR 2 861 080). Preferably, an antibody with a glycosylation profile providing enhanced cell-mediated effector functions is obtained by expressing said antibody in a cell line producing naturally unfucosilated antibodies, such as for example, an avian cell, preferably a duck cell. Particularly interesting is the production of an antibody of the invention in an avian embryonic derived stem cell line EBx® marketed by Vivalis (Nantes, France) as described in WO 2008/142124, which will provide the antibody with an optimized ADCC activity. Furthermore, an antibody produced in the avian embryonic derived stem cell line EBx® will display a human-like glycosylation pattern.

Thus, according to a preferred embodiment, an antibody of the invention has an optimized ADCC activity. Preferably, said antibody has been produced in an avian embryonic derived stem cell line EBx® and thus, has a glycosylation profile providing it with enhanced cell-mediated effector functions. More preferably, the avian embryonic derived stem cell line EBx® is from chicken or duck, and more preferably are chicken EB 14 cells, duck EB 66 or duck EB 24 cells, which may be genetically engineered to express recombinant proteins.

The binding proteins of the invention can be obtained or derived by a variety of ways, specifically by using well known methods for obtaining antibodies or antibody fragments, such as generation of antibodies by the use of mouse hybridomas (see, for example, Köhler et al., 1975, Nature 256, 495-97), production of chimaeric (Hardman et al., 1989, Int J Cancer., 44(3), 424-33) or humanized (Winter and Harris, 1993, Immunology Today 14 (6), 243-246) antibodies or antibody fragments by using recombinant DNA techniques. Preferably, fully human antibodies are obtained using technologies for the production of mAbs derived from human immunoglobulin gene sequences, such as, genetically engineered animals (e.g. Xenomouse® strains (Abgenix, Inc., Fremont, Canada), by using recombinant library methods, such as phage display, yeast display, ribosome display, E. coli display, etc. (See, e.g., Clackson et al., 1991, Nature 352, 624-628; Marks et al., 1991, J. Mol. Biol. 222, 581-597; Feldhaus and Siegel, 2004, J Immunol Methods. 290, 69-80; Groves and Osbourn, 2005, Expert Opin Biol Ther. 5(1), 125-135; and Jostock and Dubel, 2005, Comb. Chem. High Throughput Screen. 8, 127-133). Preferably, native human antibodies are obtained from recently developed technologies, including the use of human B cells directly by Human-Human hybridoma (Karpas et al., 2001, Proc Natl Acad Sci USA. 98(4), 1799-804), Hybrid hybridoma (Schmidt E, 2001, J Immunol Methods. 255(1-2), 93-102), B cell immortalization and cloning (Lanzavecchia et al., Curr Opin Biotech, 2007, 18, 523-8), genetic programming of immortalized B cells (Kwakkenbos et al., 2009, Nature Med 16(1):123-129) or Single-cell RT-PCR (Tiller et al., 2008, J Immunol Methods 329(1-2), 112-124; Wrammert et al., 2008, Nature 453(7195):667-71).

Particularly preferred is the generation of native human antibodies from human B cells, such as described in the Examples of the invention Accordingly, the antibody of the invention could be an antibody of animal origin (e.g. murine), a chimaeric, humanized or fully human antibody.

A problem with murine antibodies derives from the fact that there are many sequence differences between rodent immunoglobulins and human immunoglobulins (Kabat E A, Wu T T, Perry H M, et al. Sequences of proteins of immunological interest. US Department of Health and Human Services, U.S. Government Printing Office, 1991.). Consequently, use of rodent monoclonal antibodies into a human recipient usually results in an antiglobulin response, detectable at about 8-12 days with a peak at about 20-30 days (Isaacs J D. The antiglobulin response to therapeutic antibodies. Seminars in Immunology 1990; 2: 449-456). The presence of this immunological response will usually render the treatment inoperative after 10 days. Furthermore, later retreatment is not possible, due to the rapid onset of a secondary response.

In order to avoid immune response from the patient, is thus important to use monoclonal antibodies that are as near as possible to human antibodies. Thus, by re-engineering and de-immunization techniques chimaeric antibodies and humanized antibodies may be obtained based on murine antibodies. In a chimaeric antibody, the whole of the variable regions of a mouse or rat (or of a non-human) antibody are expressed along with human constant regions. This will lead to an antibody with proper human effector functions, while decreasing the immunogenicity caused by the xenogeneic Fc region. In a humanized antibody, only the CDR's from the rodent antibody V-regions are combined with framework regions from human V-regions. It is expected that these antibodies should thus be less immunogenic than chimaeric antibodies.

In a preferred embodiment, the antibody of the invention is fully human. Preferably, the antibody of the invention is a native human antibody or antibody fragment.

A "fully human antibody" is an antibody containing exclusively human sequences. Thus, a fully human antibody shall not induce an immune response when administered to a human recipient. Preferably, a human antibody of the invention is a "native human antibody", in which the antibody is naturally occurring in a human, as opposed to a human antibody in which the individual heavy and light chains are isolated from humans but are assembled randomly (i.e. by using library methods such as phage display) creating all forms of natural and unnatural antibodies.

Specifically, "native human antibodies" are those that arise naturally as the result of the functioning of an intact human immune system. The utility of native antibodies for the treatment of human viral diseases has been established through experience with hyperimmune human globulins. Native antibodies, as a class, differ in some respects from those obtained by library methods (phage or transgenic mouse) and possess distinct properties that may make them ideal therapeutics for human diseases. (See Dessain et ah, Exploring the Native Human Antibody Repertoire to Create Antiviral Therapeutics in Current Topics in Microbiology and Immunology 317: 155-183 (2008), (c) Springer-Verlag New York). Specifically, there is a specific advantage of native antibodies expressed from human B cells over phage-derived antibodies, due to the limitations in a phage approach to recreate all of the original or native heavy chain: light chain pairings, thus preventing important antibody structures from being incorporated into a phage-generated library. The term "native human antibodies" includes "native human antibody fragments" as described herein and in particular, Fv fragments (including derivatives thereof such as scFv and dsFv), Fab fragments, Fab' fragments or F(ab')$_2$ fragments. Specifically, the binding site of these "native human antibody fragments" will correspond to that of a native human antibody (i.e., particular combination of heavy and light chain sequences naturally occurring in a human).

Human antibodies of the invention, however, may contain residues or modifications (such as post-translational modifications) not found in a naturally occurring human antibody, including those modifications and variant sequences described herein. These modifications are typically made to further refine or enhance antibody desired properties, such as those providing a better performance, increased antibody life-time, increased stability, increased ADCC activity, etc.

In addition, the binding proteins of the invention preferably neutralize Chikungunya virus infectivity. Accordingly, in a further preferred embodiment, the invention relates to a binding protein of the invention having Chikungunya virus neutralizing activity. This may be achieved by preventing the attachment of Chikungunya virus to its receptors on host cells or inhibition of the release of RNA into the cytoplasm of the cell or prevention of RNA transcription or translation.

Preferably, the binding proteins of the invention may also be capable of neutralizing other genotypes of the genus *alphavirus*. Furthermore, the binding proteins of the invention may even be capable of neutralizing infectivity of viruses other than alphaviruses of the Togaviridae family, such as those belonging to the genus *rubivirus* or others. Further information on the Togaviridae family and its taxonomic structure and members can be found on the Index of Viruses—Togaviridae (2006). In: ICTVdB—The Universal Virus Database, version 4. Büchen-Osmond, C (Ed), Columbia University, New York, USA.

The binding proteins of the invention may prevent Chikungunya virus from infecting host cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to infection of host cells by Chikungunya virus in the absence of said binding proteins. The neutralizing activity of the binding protein may be measured, for instance, by a standard plaque reduction neutralization test (PRNT) as shown in Example 4 and FIG. 3 or by other in vitro neutralization assays, such as rapid fluorescent focus inhibition test (RFFIT), (Vene et al., 1998, Journal of Virological Methods 73(1), Pages 71-75). The neutralizing activity could also be investigated by analyzing the cell supernatant for the presence of Chikungunya viral genome by quantitative real time PCR (qRT-PCR).

Alternatively, the binding protein may be characterized in that it has a Chikungunya virus neutralizing activity of at least 2500 IU/ring protein. More preferably, said binding protein has a Chikungunya virus neutralizing activity of at least 2800 IU/ring protein, at least 3000 IU/ring protein, at least 3200 IU/ring protein, at least 3400 IU/ring protein, at least 3600 IU/ring protein, at least 3800 IU/ring protein, at least 4000 IU/ring protein, at least 4200 IU/ring protein, at least 4400 IU/ring protein, at least 4600 IU/ring protein, at least 4800 IU/ring protein, at least 5000 IU/ring protein, at least 5200 IU/ring protein, at least 5400 IU/ring protein. The neutralizing activity of the binding protein may be measured, for instance, by as standard plaque reduction neutralization test (PRNT) as shown in Example 4 and FIG. 3 or by other in vitro neutralization assays, such as rapid fluorescent focus inhibition test (RFFIT), (Vene et al., 1998, Journal of Virological Methods 73(1), Pages 71-75). The neutralizing activity could also be investigated by analyzing the cell supernatant for the presence of Chikungunya viral genome by quantitative real time PCR (qRT-PCR).

In a preferred embodiment, the neutralizing protein of the invention is selected from the anti-CHIKV neutralizing fully human antibodies shown in the Examples (8I310F8, 5F10F175E2, rec8B10F8 and rec5F10F175E2). More preferably, from the IgG1 type recombinant antibodies rec8B10F8 and rec5F10F175E2 which are characterized in Example 4.

Functional Variants

A second aspect of the invention includes functional variants of binding proteins as defined herein.

The term "functional variant", as used herein, refers to a binding molecule that comprises a nucleotide and/or amino acid sequence that is altered by one or more nucleotides and/or amino acids compared to the nucleotide and/or amino acid sequences of the parent binding protein and that is still capable of competing for binding to the binding partner, e.g. Chikungunya virus or a fragment thereof, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e. the binding molecule is still able to recognize and bind its target. Whether a modification in the amino acid sequence results in a functional binding protein (i.e. in a binding protein that binds to Chikungunya virus or a fragment thereof), can readily be determined by assaying the specific activity of the resulting binding protein in ELISA or FACS for binding to Chikungunya virus or a fragment thereof or other in vitro or in vivo functional assay. Preferably, the functional variants should also have Chikungunya virus neutralizing activity.

The functional variant may preferably have conservative sequence modifications including nucleotide and amino acid substitutions, additions and deletions. Furthermore, functional variants can comprise truncations of the amino acid sequence at either or both the amino or carboxy termini. These modifications can be introduced by standard techniques known in the art, such as site-directed mutagenesis and random PCR-mediated mutagenesis, and may comprise natural as well as non-natural nucleotides and amino acids.

Non-natural amino acids may include, for example, stereoisomers (e.g. D-amino acids) of the 20 conventional amino acids, unnatural amino acids such as α-,α-disubstituted amino acids, N-alkyl amino acids, lactic acid, and other unconventional amino acids. Examples of unconventional amino acids, which may also be suitable components for the binding protein of the invention, include: 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids, e.g. 4-hydroxyproline.

Especially preferred variations in the nucleotide or amino acid sequences shown in SEQ ID NOs: 1-46 are those that lead to a reduced susceptibility to proteolysis or oxidation, alter glycosylation patterns or alter binding affinities or confer or modify other physicochemical or functional properties of the binding protein. In particular, conservative amino acid replacements are contemplated. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). It will be clear to the skilled artisan that other classification of amino acid residue families than the one used above can also be employed. Furthermore, a variant may have non-conservative amino acid substitutions, e.g., replacement of an amino acid with an amino acid residue having different structural or chemical properties. Similar minor variations, may also include amino acid deletions or insertions, or both. Guidance in determining which amino acid residues may be substituted, inserted, or deleted without abolishing immunological activity may be found using computer programs well known in the art.

Functional variants according to the invention may have the same or different, either higher or lower, binding affinities compared to the parent binding molecule but are still capable of binding to Chikungunya virus or a fragment thereof and preferably, still capable of neutralizing Chikungunya virus. For instance, functional variants according to the invention may have increased or decreased binding affinities for Chikungunya virus or a fragment thereof compared to the parent binding proteins or may have a higher or lower Chikungunya virus neutralizing activity. Preferably, the amino acid sequences of the variable regions, including, but not limited to, framework regions, hypervariable regions, in particular the CDR3 regions, are modified. Functional variants intended to fall within the scope of the present invention have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and in particular at least about 97% to about 99% amino acid sequence identity with the parent binding proteins as defined herein. Computer algorithms such as inter alia Gap or Bestfit known to a person skilled in the art can be used to optimally align amino acid sequences to be compared and to define similar or identical amino acid residues.

Moreover, functional variants also include derivatives that are substantially similar in primary structural sequence, but which contain e.g. in vitro or in vivo modifications, chemical and/or biochemical, that are not found in the parent binding protein. Such modifications include inter alia acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, ubiquitination, and the like.

Immunoconjugates

The binding protein or a functional variant of the invention may be coupled to at least one labeling and/or effector group. Thus, in yet a further aspect, the invention includes immunoconjugates, i.e. a binding protein or a functional variant of the invention which is coupled to at least one labeling and/or effector group.

In one embodiment of the invention, a binding protein or a functional variant of the invention is coupled to at least one effector group. Such an immunoconjugate is especially suitable for therapeutic applications. As used herein, the term "effector group" refers to a therapeutic group, a toxin, a cytotoxic group, an antigen or other effector group known in the art. In a particular embodiment, a binding protein or a functional variant of the invention may be conjugated/attached to one or more antigens. Preferably, these antigens are antigens which are recognized by the immune system of a subject to which the binding molecule-antigen conjugate is administered to. The antigens may be identical but may also differ from each other. In another particular embodiment, said effector group is a therapeutic agent. Preferably, said therapeutic agent is suitable for the treatment of a viral infection or the symptoms associated to a viral disease, such as chloroquine phosphate, paracetamol, NSAID's (e.g., ibuprofen, naproxen, etc.) or corticosteroids. More preferably, said therapeutic agent is an anti-viral such as ribavirin or interferon-alpha or acyclovir. Alternatively, said therapeutic agent is useful for treating secondary effects related to the binding protein or functional variant of the invention. In certain respects, it may be desirable that the effector groups are attached by spacer arms of various lengths to reduce potential steric hindrance.

In another embodiment of the present invention, a binding protein or a functional variant of the invention is coupled to at least one labelling group. Such an immunoconjugate is particularly suitable for diagnostic applications, for example, assess if a subject has been infected with Chikungunya virus or monitor the development or progression of Chikungunya virus infection as part of a clinical testing procedure to, e.g., determine the efficacy of a given treatment regimen. However, they may also be used for other detection and/or analytical and/or diagnostic purposes. As used herein, the term "labelling group" refers to a detectable marker, e.g. a radiolabeled amino acid or biotinyl moiety that can be detected by marked avidin (e.g. streptavidin bound to a fluorescent marker or enzymatic activity that can be detected by optical or colorimetric methods). Various methods for labelling polypeptides and glycoproteins, such as antibodies, are known in the art and may be used in performing the present invention. Examples of suitable labelling groups include, but are not limited to, the following: radioisotopes or radionuclides (e.g. $^3$H, $^{14}$C, $^{15}$N, $^{35}$S, $^{90}$Y, $^{99}$Tc, $^{111}$In, $^{125}$I, $^{131}$I), fluorescent groups (e.g. FITC, rhodamine, lanthanide phosphors), enzymatic groups (e.g. horseradish peroxidase, β-galactosidase, luciferase, alkaline phosphatase), chemiluminescent groups, biotinyl groups, or predetermined polypeptide epitopes recognized by a secondary reporter (e.g. leucine zipper pair sequences, binding sites for secondary antibodies, metal binding domains, epitope tags). In certain respects, it may be desirable that the labelling groups are attached by spacer arms of various lengths to reduce potential steric hindrance.

The labeling groups used to label the binding protein or the functional variant of the invention for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISA's), radioimmunoassays (RIA's), bioassays (e.g., neutralization assays), Western blotting applications, etc.

When the binding proteins or functional variants of the invention are used for in vivo diagnostic use, said binding molecules can also be made detectable by conjugation to e.g. magnetic resonance imaging (MRI) contrast agents, such as gadolinium diethylenetriaminepentaacetic acid, to ultrasound contrast agents or to X-ray contrast agents, or by radioisotopic labeling.

Also contemplated in the present invention are mixtures of immunoconjugates according to the invention or mixtures of at least one of said immunoconjugates according to the invention and another molecule, such as a therapeutic agent or another binding molecule. In a further embodiment, the immunoconjugates of the invention may comprise one or more label and/or effector group. These can be the same or distinct from each other and can be joined/conjugated non-covalently to the binding molecules. The labelling and/or effector group (s) can also be joined/conjugated directly to the binding molecules through covalent bonding, including, but not limited to, disulfide bonding, hydrogen bonding, electrostatic bonding, recombinant fusion and conformational bonding. Alternatively, these can be joined/conjugated to the binding molecules by means of one or more linking compounds. Techniques for conjugating said groups to binding molecules are well known to the skilled artisan.

Furthermore, the binding proteins, functional variants thereof or immunoconjugates of the invention (i.e., binding molecules of the invention) can also be attached to solid supports, which are particularly useful for in vitro immunoassays or purification of Chikungunya virus or a fragment thereof. Such solid supports might be porous or nonporous, planar or nonplanar and include, but are not limited to, glass, cellulose, polyacrylamide, nylon, polystyrene, polyvinyl chloride or polypropylene supports. The binding molecules of the invention can also for example usefully be conjugated to filtration media, such as NHS-activated Sepharose or CNBr-activated Sepharose for purposes of immunoaffinity chromatography. They can also usefully be attached to paramagnetic microspheres, typically by biotin-streptavidin interaction. The microspheres can be used for isolation of Chikungunya virus or a fragment thereof from a sample containing Chikungunya virus or a fragment thereof. As another example, the binding molecules of the present invention can usefully be attached to the surface of a microtiter plate for ELISA.

Nucleic Acid Molecules

Another aspect of the present invention relates to an isolated nucleic acid molecule encoding a binding protein, a functional variant, an immunoconjugate of the invention or a fragment thereof. Preferably, the nucleic acid molecule comprises one of the nucleotide sequences of SEQ ID NO: 1, 3, 5, 7, 9, 11, 13, 15, 17, 19, 21, 23, 25, 27, 29, 31, 33, 35, 37, 39, 41, 42, 43, 44, 45 or 46.

In one embodiment, the isolated nucleic acid molecule of the invention comprises a nucleotide sequence encoding a heavy chain amino acid sequence of a binding protein of the invention comprising at least one of the sequences selected from the group consisting of SEQ ID NOs: 9, 11, 13, 29, 31, 33 or 46. Preferably, the nucleic acid molecule of the invention comprises a nucleotide sequence of SEQ ID NO: 13 or 33.

In another embodiment, the isolated nucleotide molecule of the invention comprises a nucleotide sequence encoding a light chain amino acid sequence of a binding protein of the invention comprising at least one of the sequences selected from the group consisting of SEQ ID NOs: 15, 17, 19, 35, 37 or 39.

In another embodiment, the isolated nucleic acid molecule of the invention comprises a nucleotide sequence encoding a heavy chain amino acid sequence of a binding protein of the invention comprising the sequences of SEQ ID NOs: 9 or 29, and SEQ ID NOs: 11 or 31 and SEQ ID NOs: 13 or 33. In a further embodiment, the nucleic acid molecule of the invention comprises a nucleotide sequence encoding a light chain amino acid sequence of a binding protein of the invention comprising the sequences of SEQ ID NOs: 15 or 35, and SEQ ID NOs: 17 or 37 and SEQ ID NOs: 19 or 39.

In a further embodiment, the isolated nucleic acid molecule of the invention comprises a nucleotide sequence encoding a heavy chain amino acid sequence of a binding protein of the invention comprising a sequence selected from the group consisting of SEQ ID NO: 5, 25 or 45. In another embodiment, the nucleic acid molecule of the invention comprises a nucleotide sequence encoding a heavy chain amino acid sequence of a binding protein of the invention comprising a sequence of SEQ ID NO: 1, 21, 41 or 43.

In an even further embodiment, the isolated nucleic acid molecule of the invention comprises a nucleotide sequence encoding a light chain amino acid sequence of a binding protein of the invention comprising a sequence selected from the group consisting of SEQ ID NO: 7 and 27. In another embodiment, the nucleic acid molecule of the invention comprises a nucleotide sequence encoding a light chain amino acid sequence of a binding protein of the invention comprising a sequence of SEQ ID NO: 3, 23, 42 or 44.

Within the context of the present invention, the term "isolated nucleic acid molecule", as used herein, means a polynucleotide of genomic, cDNA, or synthetic origin or some combination thereof, which by virtue of its origin, the "isolated nucleic acid molecule" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Further, the term "nucleic acid molecule", as referred to herein, means a polymeric form of nucleotides of at least 10 bases in length, either ribonucleotides or deoxynucleotides, or a modified form of either type of nucleotide, such as nucleotides with modified or substituted sugar groups and the like. The term also includes single and double stranded forms of DNA.

In a one embodiment of the present invention, a nucleic acid molecule of the invention is operably linked to a control sequence. The term "control sequence", as used herein, refers to polynucleotide sequences that are necessary to effect the expression and processing of coding sequences to which they are ligated. The nature of such control sequences differs depending upon the host organism. In prokaryotes, such control sequences generally include promoters, ribosomal binding sites, and transcription termination sequences. In eukaryotes, generally, such control sequences include promoters and transcription termination sequences. In accordance with the present invention, the term "control sequence" is intended to include, at a minimum, all components whose presence is essential for expression and processing, and can also include additional components whose presence is advantageous, for example, leader sequences and fusion partner sequences. Furthermore, the term "operably linked", as used herein, refers to positions of components so described which are in a relationship permitting them to function in their intended manner. Moreover, according to the present invention, an expression control sequence operably linked to a coding sequence is ligated in such a way that expression of the coding sequence is achieved under conditions compatible with the expression control sequence.

Vector

A further aspect of the present invention is a vector comprising one or more nucleic acid molecule that encodes a binding protein, functional variant or immunoconjugate of the invention. Vectors may be autonomously replicating or may replicate together with the chromosome into which they have been integrated. The nucleic acid molecule can be operably linked to a control sequence. Furthermore, the vector may additionally contain a replication origin or a selection marker gene. Examples of vectors that may be used in accordance with the present invention are e.g. plasmids, cosmids, phages, viruses, etc., Vectors can be used for cloning and/or for expression of the binding molecules of the invention.

Preferably, said vectors are used in eukaryotic cells, preferably, in mammalian cells. Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See for example, WO 94/11026 and the expression vector disclosed therein.

Host

Another aspect of the present invention relates to hosts containing one or more copies of the nucleic acid molecules or vectors mentioned above. Preferably, the hosts are host cells. Host cells include, but are not limited to, cells of mammalian, plant, insect, fungal or bacterial origin. Transformation could be done by any known method for introducing polynucleotides into a host cell, including for example packaging the polynucleotide in a virus (or into a viral vector) and transducing a host cell with the virus (or vector) or by transfection procedures known in the art, as exemplified by U.S. Pat. No. 4,399,216, U.S. Pat. No. 4,912,040, U.S. Pat. No. 4,740,461, and U.S. Pat. No. 4,959,455, which patents are hereby incorporated herein by reference. Particularly, methods for introducing heterologous polynucleotides into host cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. Examples of host cells that may be used according to the present invention include but are not limited to eukaryotic cells such as mammalian cells, e.g. hamster, rabbit, rat, pig, mouse, etc.; avian cells, e.g. duck, chicken, quail, etc.; insect cells or other animal cells; plant cells and fungal cells, e.g. corn, tobacco, *Saccharomyces cerevisiae*, *Pichia pastoris*; prokaryotic cells such as *E. coli*; and other cells used in the art for the production of antibodies and other binding proteins. Especially mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g. Hep G2), and a number of other cell lines. Preferably, the host cells are human cells. Examples of human cells are inter alia HeLa, 911, AT1080, A549, 293 and HEK293T cells. In another preferred embodiment, the host cells are non-immortalized cell lines, more preferably avian embryonic stem cells. Particularly preferred host cells are avian embryonic derived stem cell lines marketed under the trademark EBx® by Vivalis (Nantes, France). The avian embryonic derived stem cell lines EBx® are described, for example, in WO 03/076601 and in WO 2008/142124 which are hereby incorporated by reference. The avian embryonic derived stem cell lines EBx® are able to proliferate, in adherence or non-adherence conditions, in a basal medium in absence of growth factors, serum and/or feeder cells. Accordingly, EBx® cell lines are especially suitable for its industrial use in the obtaining of molecules of interest, in particular for the production of viral vaccines or proteins (e.g. the binding protein or functional variant of the present invention). Preferably, the EBx® cells are from chicken or duck, and more preferably are chicken EB 14 cells, duck EB 66 or duck EB 24 cells. Furthermore, as described in WO 2008/142124, antibodies expressed in avian embryonic derived stem cell line EBx®, e.g., EB 66 cell line, have a glycosylation profile providing the antibody with enhanced cell-mediated effector functions. Furthermore, said antibody will display a human-like glycosylation pattern.

A Process for Producing the Binding Protein, Functional Variant or Immunoconjugate of the Invention A further aspect of the present invention relates to a method for producing a binding protein, functional variant or immunoconjugate of the invention (i.e., binding molecules of the invention) by preparing said molecule(s) of the invention from a host cell that secretes said molecule(s). Examples of host cells that may be used according to the present invention include but are not limited to eukaryotic cells such as mammalian cells, e.g. hamster, rabbit, rat, pig, mouse, etc.; avian cells, e.g. duck, chicken, quail, etc.; insect cells or other animal cells; plant cells and fungal cells, e.g. corn, tobacco, *Saccharomyces cerevisiae*, *Pichia pastoris*; prokaryotic cells such as *E. coli*; and other cells used in the art for the production of antibodies and other binding proteins as above described. Various methods for preparing and isolating binding proteins, such as scaffold proteins or antibodies, from host cells are known in the art and may be used in performing the present invention. Moreover, methods for preparing binding protein fragments, e.g. scaffold protein fragments or antibody fragments, such as papain or pepsin digestion, modem cloning techniques, techniques for preparing single chain antibody molecules (Pluckthun in: The Pharmacology of Monoclonal Antibodies 113, Rosenburg and Moore, EDS, Springer Veriag, N.Y. (1994), 269-315) and diabodies (Hollinger et al., 1993, Proc. Natl. Acad. ScL U.S.A. 90, 6444-6448), are also known to those skilled in the art and may be used in performing the present invention.

In one embodiment of the present invention, a binding protein, functional variant or immunoconjugate of the invention is prepared from a hybridoma that secretes the binding protein. See e.g. Köhler et al., 1975, Nature 256, 495-97.

In a preferred embodiment of the present invention, the binding protein, functional variant or immunoconjugate of the invention (i.e., binding molecules of the invention) is prepared recombinantly by optimizing and/or amplifying expression of the binding molecule of the invention in a host cell and isolating the binding molecule from said host cell. To this end, the host cells are transformed or transfected with DNA encoding a binding protein or a vector containing DNA encoding the binding molecule and cultured under appropriate conditions to produce the binding molecule of the invention, see for example, U.S. Pat. No. 4,816,567.

Another aspect of the present invention relates to a method for producing a binding protein, functional variant or immunoconjugate of the invention (binding molecules of the invention) by preparing said binding molecule of the invention from a tissue, product or secretion of an animal, plant or fungus transgenic for a nucleic acid molecule or nucleic acid molecules encoding the molecule(s) of the invention. Preferably, a binding protein, functional variant or immunoconjugate of the invention is prepared from the tissue, product or secretion of a transgenic animal such as cow, sheep, rabbit, chicken or other mammalian or avian species, a transgenic plant such as corn, tobacco or other plant, or a transgenic fungus such as *Aspergillus*, *Pichia* or other fungal species.

Nucleic Acid Molecule Compositions

In yet a further aspect, the invention provides compositions comprising at least one nucleic acid molecule as defined in the present invention. The compositions may comprise aqueous solutions such as aqueous solutions containing salts (e.g., NaCl or salts as described above), detergents (e.g., SDS) and/or other suitable components.

Pharmaceutical Compositions

Furthermore, in an additional aspect the present invention relates to pharmaceutical compositions comprising at least one binding protein, at least one functional variant, at least one immunoconjugate or at least one composition according to the invention, or combinations thereof, and a pharmaceutically acceptable carrier, excipient, or stabilizer (Remington's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions.

In accordance with the present invention, acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; surfactant such as polysorbate; salt-forming counterions such as sodium; metal complexes (e.g. Zn-protein complexes); and/or non-ionic surfactants such as TWEEN™, PLURONICS™ or polyethylene glycol (PEG).

RNA viruses such as Chikungunya virus make use of their own RNA polymerase during virus replication. These RNA polymerases tend to be error-prone. This leads to the formation of so-called quasi-species during a viral infection.

Each quasi-species has a unique RNA genome, which could result in differences in amino acid composition of viral proteins. If such mutations occur in structural viral proteins, the virus could potentially escape from the host's immune system due to a change in T or B cell epitopes.

Accordingly, in a preferred embodiment the pharmaceutical composition according to the invention comprises at least one additional binding protein, functional variant or immunoconjugate of the invention (binding molecules of the invention), i.e. the pharmaceutical composition can be a cocktail/mixture of binding molecules of the invention. The pharmaceutical composition may comprise at least two binding molecules according to the invention or at least one binding molecule according to the invention and at least one further anti-CHIKV virus binding molecule. The binding molecules in the pharmaceutical composition should preferably be capable of reacting with different, non-competing epitopes of the Chikungunya virus, thus, minimizing the chance of the occurrence of Chikungunya escape viruses. Epitopes may be present for example on the E1 or E2 glycoproteins of Chikungunya virus and may be different, non-overlapping epitopes. The binding molecules should preferably be of high affinity and should preferably have a broad specificity. More preferably, they neutralize as many strains of Chikungunya virus as possible. Even more preferably, they also exhibit neutralizing activity towards other genotypes of the genus *alphavirus* or even with other viruses of the Togaviridae family, while exhibiting no cross-reactivity with other viruses or normal cellular proteins. Preferably, one of the binding molecules is capable of neutralizing escape variants of the other binding molecule in the cocktail.

In a preferred embodiment, the present invention relates to a pharmaceutical composition comprising at least two Chikungunya virus neutralizing binding molecules, preferably binding molecules according to the invention, characterized in that the binding molecules are capable of reacting with different, non-competing epitopes of the Chikungunya virus. In an embodiment the pharmaceutical composition comprises a first Chikungunya virus neutralizing binding molecule which is capable of reacting with an epitope located in an antigenic site of one of the Chikungunya virus envelope proteins (E1 or E2) and a second Chikungunya virus neutralizing binding molecule which is capable of reacting with an epitope located in a different antigenic site of the same Chikungunya virus envelope protein (e.g. E2) or alternatively in an antigenic site of the other envelope glycoprotein (e.g. E1). Epitope mapping and identification of the antigenic site can be performed by methods well known in the art, such as using truncated and/or mutated forms of recombinant virus protein(s), identification of the nucleotide substitution(s) in viral escape mutants, if any (Gal-Tanamy et al., 2008, PNAS 105(49):19450-19455), or crystal structure analysis of the antibody-antigen complex (Lescar et al., 1995, J Biol Chem 270(30):18067-76). Epitope mapping could also be performed by competition ELISA as described in The Protein Protocols Handbook (1996), p 595-600).

Furthermore, the pharmaceutical composition according to the invention may comprise at least one other therapeutic and/or prophylactic agent for the particular indication, e.g. infection being treated, or to prevent undesired effects. Preferably, the additional therapeutic and/or prophylactic agent has an activity complementary to that of the binding molecule, functional variant, immunoconjugate or composition according to the invention and do not adversely affect each other. In particular, said further therapeutic and/or prophylactic agent can be an agent suitable for the treatment of a viral infection or suitable for the treatment of the symptoms associated to a viral infection, such as chloroquine phosphate, paracetamol, NSAID's (e.g., ibuprofen, naproxen, etc.) or corticosteroids. More preferably, said therapeutic agent is an anti-viral such as ribavirin, acyclovir or interferon-alpha, or a vaccine against an *alphavirus*, in particular against the Chikungunya virus. Alternatively, said therapeutic agent is useful for treating secondary effects related to the binding protein, functional variant or immunoconjugate of the invention.

The active ingredients, e.g., binging molecules, functional variants or immunoconjugates of the present invention and other therapeutic agents, may be entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nano-particles and nanocapsules) or in macroemulsions. Such techniques are disclosed for example in Remington's Pharmaceutical Sciences 16th edition, Osol, A. Ed. (1980).

The pharmaceutical composition of the invention will be formulated according to the chosen route of administration. The pharmaceutical composition of the invention can be administrated by any suitable route, including but not limited to oral, rectal, transdermal, ophthalmic, nasal, topical, vaginal or parenteral. In a particular embodiment, the pharmaceutical composition is formulated in order to be suitable for parenteral administration to a patient, e.g., a human being, preferably by intravenous, intramuscular, intraperitoneal or subcutaneous administration. Illustrative, non limiting examples of suitable formulations for parenteral administration are solutions, suspensions, emulsions, lyophilized compositions and the like.

Furthermore, sustained-release compositions are also contemplated. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxyburyric acid.

The administration of the pharmaceutical composition of the invention to the patient in need thereof can be carried out by conventional means and delivery will take place using the appropriate equipments, apparatus, and devices which are known by the skilled person in art. The term "patient", as used herein, refers to a mammalian patient, i.e. any animal classified as a mammal, including humans, domestic and farm animals, and zoo, sports, or pet animals, such as dogs, cats, cattle, horses, sheep, pigs, goats, rabbits, etc. Preferably, the patient in need of treatment is a human patient.

The dosage and schedule of administration of the pharmaceutical composition of the invention will vary according to the particular formulation, the mode of administration, and the particular situs and infection being treated. Other factors like age, body weight, sex, diet, rate of excretion, condition of the subject, drug combinations, reaction sensitivities and severity of the infection shall be taken into account. Generally, a therapeutically effective amount of a binding molecule, functional variant or immunoconjugate of the invention is administered to a patient. The term "therapeutically effective amount" refers to an amount of drug effective to "prevent or treat" a disease or disorder in a patient, as defined below.

In particular embodiments, the amount of molecule administered will typically be in the range of about 0.01 mg/kg to about 50 mg/kg of patient body weight. Depending on the type and severity of the infection, about 0.01 mg/kg to about 50 mg/kg body weight of a molecule of the invention can be an initial candidate dosage for administration to the patient, whether, for example, by one or more separate administrations, or by continuous infusion. The progress of this therapy can be readily monitored by conventional methods and assays and based on criteria known to the physician or other persons of skill in the art.

Therapeutic Uses

In a further aspect, the binding proteins, functional variants, immunoconjugates, compositions, or pharmaceutical compositions of the invention can be used as a medicament. In particular, the binding proteins, functional variants, immunoconjugates, compositions, or pharmaceutical compositions of the invention may be used in the prevention or treatment of an arbovirus infection. Preferably this arbovirus is a virus of the Togaviridae family, more preferably this virus is an *alphavirus*. The *alphavirus* can be a virus from any of the known genotypes, but is preferably a Chikungunya virus.

In accordance with the present invention, the term "prevention or treatment", when used herein, refers to both therapeutic treatment and prophylactic or preventative measures, wherein the patient in need is to prevent or slow down (lessen) the targeted pathologic condition or disorder. Those in need of prevention or treatment include those already with the disorder as well as those prone to have the disorder or those in whom the disorder is to be prevented. The patient in need of prevention or treatment is a mammalian patient, i.e. any animal classified as a mammal, including humans, domestic and farm animals, and zoo, sports, or pet animals, such as dogs, cats, cattle, horses, sheep, pigs, goats, rabbits, etc. Preferably, the patient in need of treatment is a human patient.

In a preferred embodiment, a binding protein, functional variant or immunoconjugate of the invention (binding molecules of the invention) with an optimized ADCC activity is used in the prevention or treatment of an arbovirus infection. Preferably this arbovirus is a virus of the Togaviridae family, more preferably an *alphavirus*. The *alphavirus* can be a virus from any of the known genotypes, but is preferably a Chikungunya virus. In a further preferred embodiment, said binding molecule of the invention is an antibody with a glycosylation profile providing it with enhanced cell-mediated effector functions. Preferably, said antibody of the invention has been obtained by expression in a cell line producing naturally unfucosilated antibodies, such as for example, an avian cell, preferably a duck cell. Preferably this binding molecule has been produced in avian embryonic derived stem cell line EBx® marketed by Vivalis (Nantes, France), as described for example in WO 2008/142124.

In a further aspect of the invention, binding proteins, functional variants, immunoconjugates, compositions, or pharmaceutical compositions of the invention can be used with other drugs to provide a combination therapy for the treatment of an arbovirus infection, as above described. The other drugs may form part of the same composition, or be provided as a separate pharmaceutical composition for administration at the same time or at a different time.

The identity of the other drug is not particularly limited. In a particular embodiment, said additional drug is administered simultaneously or sequentially to the binding proteins, functional variants, immunoconjugates, compositions, or pharmaceutical compositions of the invention, spaced out in time, in any order, i.e. first the molecules or compositions of the invention, then the additional drug can be administered, or first the additional drug and then the molecules or compositions of the invention. In another alternative embodiment the molecules or compositions of the invention and an additional drug are simultaneously administered.

Preferably, said combination therapy comprises at least two Chikungunya virus neutralizing binding molecules. More preferably said binding molecules are binding proteins, functional variants or immunoconjugates of the invention (binding molecules of the invention), characterized in that the binding molecules are capable of reacting with different, non-competing epitopes of the Chikungunya virus. The chance of the occurrence of Chikungunya escape viruses is thereby minimized. As a consequence thereof, the binding molecules of the invention preferably are capable of reacting with different, non-overlapping, non-competing epitopes of the Chikungunya virus, such as epitopes on the virus glycoproteins E1 and E2.

Alternatively, the additional drug is a drug useful in the prevention and/or treatment of a viral infection or a drug useful for reducing undesired secondary effects of the molecules or compositions of the invention. For instance, the binding molecules, functional variants, immunoconjugates or pharmaceutical compositions of the invention can be co-administered with antiviral molecules such as ribavirin or interpheron-α or with a vaccine against an *alphavirus*, in particular against the Chikungunya virus. The additional drug may also be administered before or after administration of the molecules or compositions of the invention, in any desired order.

Diagnostic Use

The invention further pertains to a method of in vitro detecting a Chikungunya virus in an isolated sample, wherein the method comprises the steps of a) contacting a sample with a diagnostically effective amount of a binding protein, a functional variant or an immunoconjugate according to the invention (i.e., binding molecules of the invention), and b) determining whether the binding molecule of the invention specifically binds to a molecule of the sample. The sample may be a biological sample including, but not limited to blood, serum, tissue or other biological material from (potentially) infected subjects. The (potentially) infected patients may be human patients, but also animals that are suspected as carriers of Chikungunya virus might be tested for the presence of Chikungunya virus using the binding molecules of the invention. The sample may first be manipulated to make it more suitable for the method of detection. Manipulation means inter alia treating the sample suspected to contain and/or containing Chikungunya virus in such a way that the Chikungunya virus will disintegrate into antigenic components such as proteins, (poly) peptides or other antigenic fragments. Preferably, the binding molecules of the invention are contacted with the sample under conditions which allow the formation of an immunological complex between the binding molecules and Chikungunya virus or antigenic components thereof that may be present in the sample. The formation of an immunological complex, if any, indicating the presence of Chikungunya virus in the sample, is then detected and measured by suitable means. Such methods include, inter alia, homogeneous and heterogeneous binding immunoassays, such as radioimmunoassays (RIA), enzyme-linked immunoassay (ELISA), immunofluorescence, immunohistochemistry, flow cytometry (e.g. FACS), surface plasmon resonance (e.g. BIACORE) and Western blot analyses. Preferably, the molecule of the invention is an immunoconjugate.

In addition, immunoconjugates of the invention may be used for example in the in vivo detection of the Chikungunya virus infection by the use of imaging and nuclear medicine techniques. Various nuclear medicine techniques are well known in the art and have been widely used for example to image foci of infection and inflammation (Corstens et al., 1993, Seminars in Nuclear Medicine 23(2), 148-164).

Screening Uses

Furthermore, the binding protein, functional variant or immunoconjugate of the invention (binding molecules of the invention) can be used to identify epitopes of Chikungunya virus proteins such as the E1 or E2 glycoproteins. The epitopes can be linear, but also structural and/or conformational. In one embodiment, binding of the binding molecules of the invention to a series of overlapping peptides, such as 15-mer peptides, of a protein from Chikungunya virus such as the Chikungunya virus E1 or E2 glycoproteins can be analyzed by means of PEPSCAN analysis (see inter alia WO 84/03564, WO 93/09872, Slootstra et al., 1996, Mol Divers. 1(2), 87-96). The binding of said binding molecules to each peptide can be tested in a PEPSCAN-based enzyme-linked immuno assay (ELISA). In another embodiment, a random peptide library comprising peptides from Chikungunya virus proteins can be screened for peptides capable of binding to the binding molecules of the invention. In the above assays the use of Chikungunya virus neutralizing binding molecules may identify one or more neutralizing epitopes. The peptides/epitopes found can be used as vaccines and for the diagnosis of Chikungunya infection.

Accordingly, in a further aspect, the invention provides a method of screening a binding molecule for specific binding to a different, preferably non-overlapping epitope of Chikungunya virus as the epitope bound by a binding molecule of the invention, wherein the method comprises the steps of a) contacting a binding molecule to be screened, a binding molecule of the invention and Chikungunya virus or a fragment thereof (such as for instance the Chikungunya virus E1 or E2 glycoproteins), b) measure if the binding molecule to be screened is capable of competing for specifically binding to the Chikungunya virus or fragment thereof with the binding molecule of the invention. If no competition is measured the binding molecules to be screened bind to a different epitope. In a specific embodiment of the above screening method, human binding molecules may be screened to identify human binding molecules capable of binding a different epitope than the epitope recognized by the binding molecule comprising the CDRH3 comprising the amino acid sequence of SEQ ID NO: 14 or 34. Preferably, the epitopes are non-overlapping or non-competing. It is clear to the skilled person that the above screening method can also be used to identify binding molecules capable of binding to the same epitope. In a further step it may be determined if the screened binding molecules that are not capable of competing for specifically binding to the Chikungunya virus or fragment thereof have neutralizing activity. It may also be determined if the screened binding molecules that are capable of competing for specifically binding to the Chikungunya virus or fragment thereof have neutralizing activity. Neutralizing anti-CHIKV virus binding molecules found in the screening method are another part of the present invention.

In the screening method "specifically binding to the same epitope" also contemplates specific binding to substantially or essentially the same epitope as the epitope bound by the binding molecules of the invention. The capacity to block, or compete with, the binding of the binding molecules of the invention to Chikungunya virus typically indicates that a binding molecule to be screened binds to an epitope or binding site on the Chikungunya virus that structurally overlaps with the binding site on the Chikungunya virus that is immunospecifically recognized by the binding molecules of the invention. Alternatively, this can indicate that a binding molecule to be screened binds to an epitope or binding site which is sufficiently proximal to the binding site immunospecifically recognized by the binding molecules of the invention to sterically or otherwise inhibit binding of the binding molecules of the invention to Chikungunya virus or a fragment thereof.

In general, competitive inhibition is measured by means of an assay, wherein an antigen composition, i.e. a composition comprising Chikungunya virus or fragments thereof (such as E1 or E2 glycoproteins), is admixed with reference binding molecules and binding molecules to be screened. In an embodiment the reference binding molecule may be one of the human binding molecules of the invention and the binding molecule to be screened may be another human binding molecule of the invention. In another embodiment the reference binding molecule may be the binding molecule comprising the CDRH3 comprising the amino acid sequence of SEQ ID NO: 14 or 34 and the binding molecule to be screened may be one of the human binding molecules of the invention. In yet another embodiment the reference binding molecule may be one of the human binding molecule of the invention and the binding molecule to be screened may be the binding molecule comprising the CDRH3 comprising the amino acid sequence of SEQ ID NO: 14 or 34.

Usually, the binding molecules to be screened are present in excess. Protocols based upon ELISAs are suitable for use in such simple competition studies. In certain embodiments, one may pre-mix the reference binding molecules with varying amounts of the binding molecules to be screened (e.g., 1:10, 1:20, 1:30, 1:40, 1:50, 1:60, 1:70, 1:80, 1:90 or 1:100) for a period of time prior to applying to the antigen composition. In other embodiments, the reference binding molecules and varying amounts of binding molecules to be screened can simply be admixed during exposure to the antigen composition. In any event, by using species or isotype secondary antibodies one will be able to detect only the bound reference binding molecules, the binding of which will be reduced by the presence of a binding molecule to be screened that recognizes substantially the same epitope.

Binding molecules identified by these competition assays ("competitive binding molecules") include, but are not limited to, antibodies, antibody fragments and other binding agents that bind to an epitope or binding site bound by the reference binding molecule as well as antibodies, antibody fragments and other binding agents that bind to an epitope or binding site sufficiently proximal to an epitope bound by the reference binding molecule for competitive binding between the binding molecules to be screened and the reference binding molecule to occur. Preferably, competitive binding molecules of the invention will, when present in excess, inhibit specific binding of a reference binding molecule to a selected target species by at least 10%, preferably by at least 25%, more preferably by at least 50%, and most preferably by at least 75%-90% or even greater. The identification of one or more competitive binding molecules that bind to about, substantially, essentially or at the same epitope as the binding molecules of the invention is a straightforward technical matter. As the identification of competitive binding molecules is determined in comparison to a reference binding molecule, it will be understood that actually determining the epitope to which the reference binding molecule and the competitive binding molecule bind is not in any way required in order to identify a competitive binding molecule that binds to the same or substantially the same epitope as the reference binding molecule. Alternatively, binding molecules binding to different non-competing epitopes identified by these competition assays may also include, but are not limited to, antibodies, antibody fragments and other binding agents.

Kits

In a further aspect, the invention relates to kits comprising at least one binding protein according to the invention, at least one functional variant thereof according to the invention, at least one immunoconjugate according to the invention, at least one nucleic acid molecule according to the invention, at least one composition according to the invention, at least one pharmaceutical composition according to the invention, at least one vector according to the invention, at least one host according to the invention or a combination thereof are also a part of the present invention. Optionally, the above described components of the kits of the invention are packed in suitable containers and labeled for diagnosis, prevention and/or treatment of the indicated conditions. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The containers may be formed from a variety of materials such as glass or plastic and may have a sterile access port (for example the container may be an intravenous solution bag or a vial having a stopper pierceable by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes and/or culture medium for one or more of the suitable hosts. Associated with the kits can be instructions customarily included in commercial packages of therapeutic, prophylactic or diagnostic products, that contain information about for example the indications, usage, dosage, manufacture, administration, contraindications and/or warnings concerning the use of such therapeutic, prophylactic or diagnostic products.

EXAMPLES

The following examples, including the experiments conducted and the results achieved, further illustrate the invention. They should not, however, be interpreted as a limitation of the scope of the invention.

Example 1

Isolation of Human mAbs Neutralizing Chikungunya Virus Infection

The purpose of this assay was to isolate human monoclonal antibodies (mAbs) capable of neutralizing Chikungunya virus from an infected individual who has naturally developed antibody protection against the virus infection. In this study, two different strains of Chikungunya Viruses (CHIKV), A226 and A226V strains, were used (both kindly provided by Dr Raymond Lin, National University Hospital, Singapore). The viral strains sequences have not yet been fully characterized except for the viral envelope protein 1 (E1) encoding sequences. One amino acid difference has been identified between the E1 protein sequences of these viral isolates at the 226 amino acid position, either an alanine (A) in the A226 strain or a valine (V) in the A226V strain.

Isolation of B Cells from an Infected Donor 50 ml of blood were obtained in ACD-A tubes (BD Biosciences, SG) from an individual (42 years-old woman) who had been infected by Chikungunya virus (CHIKV) six weeks before and had neutralizing titers of anti-Chikungunya antibodies in the plasma.

Peripheral blood mononuclear cells (PBMC), including monocytes, B and T lymphocytes, were isolated by classical Ficoll™ (GE healthcare, SG) extraction. PBMC were counted and the percentage of B lymphocyte cells was determined by flow cytometry analysis (Facscalibur, Beckton-Dickinson) after co-staining with anti-human CD45 (Mouse anti-Human CD45 Alexa Fluor 488-labeled, Invitrogen) and anti-human CD19 (Mouse anti-Human CD19 R-Phycoerythrin-labeled, Invitrogen).

Immortalization of the B Cells

The B cells were transformed with a suitable Epstein-Barr virus (EBV) strain and were immediately activated via the CD40 pathway.

The total PBMC was seeded into the wells of 96 well-plates (BD Falcon) in order to have three different densities of B cell populations: 10 B cells per well (6×96-well plates), 30 B cells per well (7×96-well plates) and 500 B cells per well (7×96-well plates). The B cells were immediately activated via the CD40 pathway, either by adding to the cell medium an antibody anti-Human CD40 (Mouse anti-CD40; Dendritics, France) at 0.5 µg/ml, or by adding to the wells 10000 lyophilized L cells (fibroblastic cells; Dendritics, France) constitutively expressing at the cell surface the CD40-ligand. The B cells were also immediately immortalized by EBV infection by adding 100 µl/well of infectious cell supernatant obtained from B95.8 cells. B95.8 is a human lymphoblastoïde cell line chronically infected by the EBV and actively producing some infectious viral particles (ATCC Number VR-1492).

The immortalized B cells were grown in Dulbecco's modified Eagle's growth medium-F12 (DMEM-F12, Invitrogen) supplemented with 10% Fetal Calf Serum (FCS, Invitrogen), 4 mM L-Glutamine (Gibco-Invitrogen), 100 U/ml of penicillin (Gibco-Invitrogen), 100 µg/ml of streptomycin (Gibco-Invitrogen) and 2% of ADCM medium (Dentritics, France).

Characterization of the Immortalized B Cell Populations by Binding and Neutralization Tests A couple of weeks after the B cells immortalization, the polyclonal B cell populations obtained were analyzed for their capacity to secrete antibodies specific for CHIKV by performing a binding test on fixed CHIKV-infected HEK 293T cells (ATCC Number CRL-N268).

Firstly, 48 h prior to undertaking the binding test on the immortalized B cell supernatants, 20000 HEK 293T cells were seeded per well of 96-well plates and 24 hours before the test, the cells were infected with A226V CHIKV strain at a Multiplicity Of Infection (MOI, or number of infectious viral particles per cell) of 0.1. The day of the test, the cells were extensively washed with phosphate buffered saline (PBS), permeabilized and fixed with an ethanol/acetone (70:30 v/v) fixation solution. The immortalized B cell supernatants were then analyzed for the presence of CHIKV-specific antibodies. For each B cells supernatant's containing well, 50 μl of the supernatant were applied to one well with CHIKV infected HEK 293T cells, and 50 μl were applied to a well with uninfected HEK 293T cells, as a negative control. The wells were incubated for 1 h at 37° C. and the binding of anti-CHIKV antibodies was then detected by immunofluorescent assay (IFA), using a cocktail of secondary antibodies consisting of anti-Human IgG (Alexa Fluor 488 goat anti-human IgG (H+L), Invitrogen) at 2 μg/ml, anti-human IgM (Alexa Fluor 488 goat anti-human IgM Invitrogen) at 2 μg/ml, and anti-human IgA (FITC-goat anti-human IgA, Invitrogen) 1/1000. Fluorescence was analyzed under a fluorescent microscope (×10 magnificence, NIKON ECLIPSE TS 100). 215 polyclonal B cell populations were identified as being specific for A226V CHIKV. Results of the binding tests are not show.

The polyclonal B cell populations identified as positive for anti-CHIKV antibodies secretion were subjected to a neutralization test with the purpose to identify those secreting antibodies neutralizing CHIKV infection in vitro. 4000 plaque forming units (PFU) of A226V CHIKV were incubated for 1 h at 37° C. with 50 μl of CHIKV-specific polyclonal B cells supernatants. As positive control, 1/40 of anti-CHIKV human plasma (isolated from the donor patient) was incubated with the same amount of PFU. 1/40 of human serum AB (Gemini Bio-products) from normal healthy male donors was used as negative control. The mixtures were then added for 1.5 hours to 40,000 HEK 293T cells, which were seeded within 96-wells plates 24 h before. 24 h after the infection, cells were extensively washed, fixed as described above, incubated for 1 h with anti-CHIKV plasma 1/200 as a primary antibody, and then incubated for 1 h with the fluorescent labeled-anti-human Ig as described above. Fluorescence was analyzed under a fluorescent microscope (×10 magnificence, NIKON ECLIPSE TS 100). 91 of the 215 polyclonal B cell populations selected for being specific for A226V CHIKV displayed neutralizing activity against A226V.

Cloning of the B Cells Secreting CHIKV Neutralizing Antibodies

The B cells secreting antibodies neutralizing CHIKV infectivity were cloned by limiting dilutions within 96-well plates (1/5 serial dilutions) and, after expansion (for 15 days), the wells containing the highest cell dilution and remaining positive for CHIKV neutralization were further amplified to a culture volume of 0.5 L. During amplification, the cells were regularly analyzed for their specificity for CHIKV, as well as for their capacity to secrete CHIKV neutralizing antibodies, by binding and neutralization tests, as described above.

Monoclonal Antibodies Purification and Ig Subclass Determination

After amplification, the monoclonal antibodies were purified from the cell culture supernatant. The monoclonal B cells were cultivated for 7 days in DMEM F12 medium supplemented as described above but without FCS, in order to avoid any presence of undesired bovine immunoglobulins. After 7 days, the cell culture supernatant was harvested, filtered on 0.45 μm membranes (Corning) and 500 ml of culture supernatant were incubated overnight with 2 ml of protein G-conjugated agarose beads (Protein G Agarose, Millipore). The protein G-beads were then extensively washed with PBS buffer and subsequently the bound antibodies were eluted with a solution of Glycine 1M (Sigma-Aldrich), pH 2.8. After elution, the acidity of the elution buffer was immediately neutralized by the volume to volume addition of Tris-base buffer pH 8 (1st Base company). The purified antibodies were then dialyzed overnight in PBS buffer, using a Slide-A-Lyzer Dialysis Cassette, 10.000 MWCO (Thermoscientific).

Two different monoclonal antibodies capable of efficiently preventing Chikungunya virus infection in vitro have been isolated. They have been named 8B10F8 and 5F10F175E2. The isotype class was determined by Flow Cytometry analysis (FACSCalibur, Beckton-Dickinson) using the Multiplex Bead Assay for Human Ig Isotyping (SouthernBiotech). Both monoclonal antibodies belong to the IgG1 subclass of immunoglobulins (results not shown).

IC50 Determination by Plaque Reduction Assay

The inhibition concentration 50 (IC50) is the antibody concentration leading to the neutralization of half of the infective viral particles. The IC50 of the two isolated human monoclonal antibodies was determined.

Serial dilutions of purified monoclonal antibodies (1/10 dilutions from 100 μg/ml to 0.1 ng/ml) were put in contact with 200 PFU (Plaque Forming Unit, in other words infectious viral particles) of CHIKV for 1 h at 37° C. and subsequently, said antibody/virus mixtures were applied onto Vero cells (ATTC CCL-81), which were seeded 24 h before within 6-well plates (BD Falcon), for 1 h at 37° C. to allow the virus to bind to the cells. After the infection step, the culture medium (DMEM (Gibco-Invitrogen) supplemented with 10% FCS) was removed and replaced by 0.25% agarose-medium (Invitrogen), this was done in order to prevent secondary infections by spreading of neo-synthesized viral particles so that the PFUs eventually quantified directly correlate with the amount of viral particles initially used for the cell infection. 48 h after infection, the agarose-medium was removed and the viable cells were stained with a cristal violet solution (Sigma-Aldrich) in order to visualize the plaques resulting from each PFU. The Plaque Reduction Assay was performed with both CHIKV strains used in the study, namely the A226 and the A226V CHIKV strains. Within one same experiment, each condition was performed in duplicate. The neutralization potency of the 5F10F175E2 and 8B10F8 monoclonal antibodies, as single agents and in combination (at the same final antibody concentration as that used in the single antibodies' determination) was determined to investigate any synergic effect of the antibody association. The experiment was performed in parallel with the irrelevant human IgG1 antibody HA4 as a negative control for neutralization. The percentage of neutralization associated to each condition was determined by the number of PFU obtained, compared to that obtain with the irrelevant human IgG1. Both antibodies (8B10F8 and 5F10F175E2) were found to have an IC50 of about 100 ng/ml as single agents. No significant synergistic effect on neutralization was observed when both antibodies were used in combination. Results are not shown.

Example 2

CHIKV Neutralizing Antibodies Sequencing

The variable domains of the heavy and light chains of the 5F10F175E2 and 8B10F8 monoclonal antibodies were sequenced by first extracting the total RNA of the corresponding monoclonal B cell populations. Total RNA was extracted using TRizol® reagent (Invitrogen) according to the provider's instructions. For each antibody, from the total RNAs, two independent reverse-transcriptions were performed using the reverse-transcriptase kit (Clontech), giving rise to 2 independent complementary DNAs (cDNAs). From each cDNA, a whole set of PCRs aiming to amplify all the possible heavy and light chains were performed using the AdvantageR 2PCR kit (Clontech). The light chains were amplified using, as a forward primer, the 5'-PCR Primer II A provided with the PCR kit (Clontech), and as reverse primers, the whole set of reverse primers specific for the different constant regions of the different possible light chains. The Heavy chains were amplified using, subtype-specific (IgG, IgM, IgA) reverse primers in conjunction with forward primers corresponding to the signal peptide regions.

Figure 2:
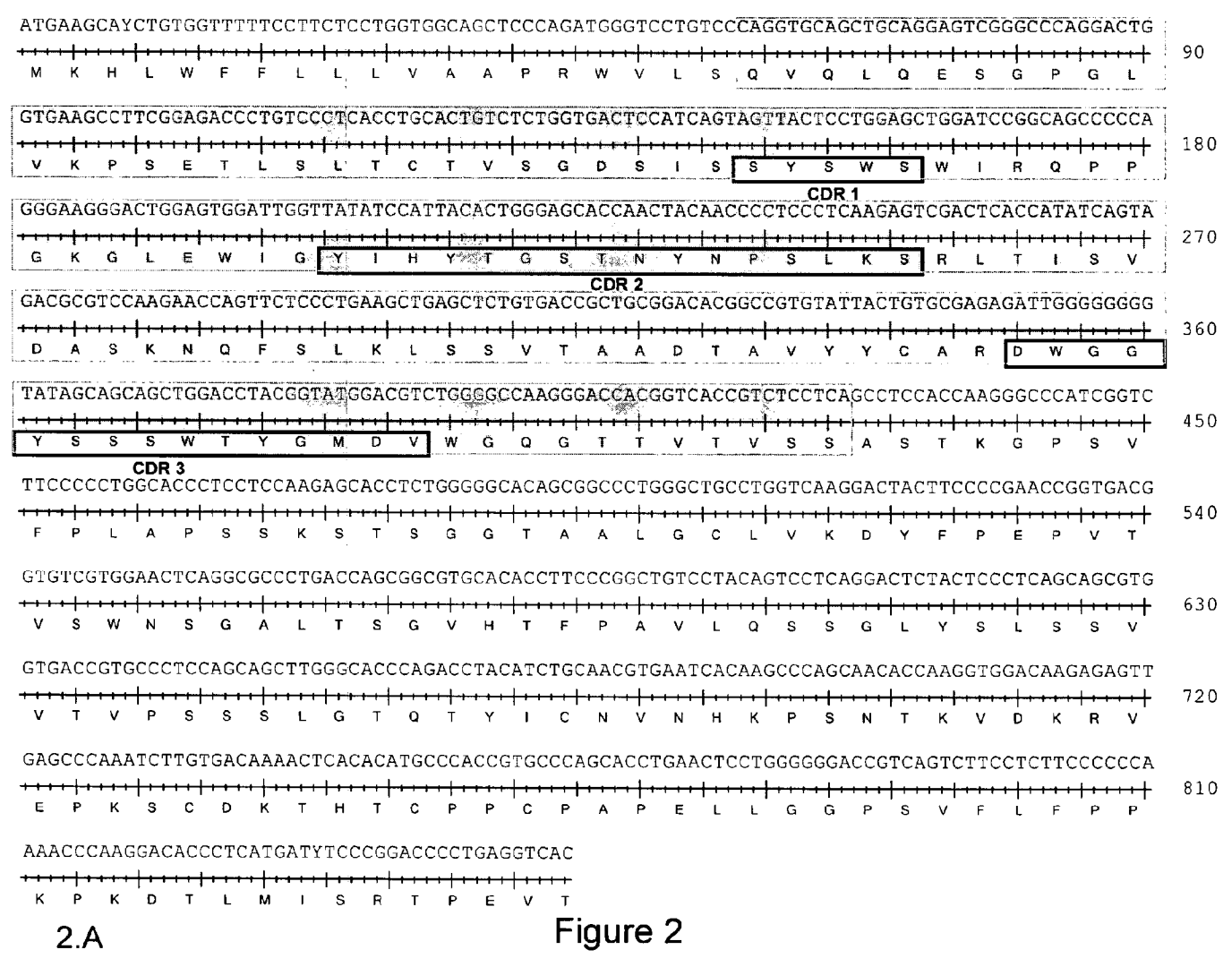

Depending on the obtained results, the same amplified fragments were mixed together and sequenced. The nucleotide sequences of the heavy and light chains of the 5F10F175E2 antibody are shown in FIGS. 2A and 2B, respectively; and the nucleotide sequences of the heavy and light chains of the 8B10F8 antibody are shown in FIGS. 3A and 3B, respectively.

Example 3

Expression of Recombinant mAbs

The nucleotide sequences encoding the variable domain of the heavy chain (VH) and the whole light chain (L), were molecularly cloned into pPMhIgG1 expression plasmid (a gift kindly provided by Dr. John Wu from ProMab), using the T4 DNA ligase (New England Biolabs) according to the provider's instructions and the ligation product was transformed into competent bacteria (Library Efficiency DHF-α, Invitrogen). The two plasmids encoding the light and the heavy chain of each antibody were co-transfected (0.5 µg/1×10$^6$ cells for each plasmid) using lipofectamin 293™ (Invitrogen) into human HEK293TPM1 cells.

Silent point mutations were introduced in the recombinant sequences to add or remove restriction enzyme sites to facilitate the cloning into the expression vector. The heavy chain and light chain cDNA sequence of rec5F10F175E2 is shown in SEQ ID NO: 41 and 42, respectively. The heavy chain and light chain cDNA sequence of rec8B10F8 is shown in SEQ ID NO: 43 and 44, respectively. The protein sequences are identical between the "isolated" (8B10F8 and 5F10F175E2) and the "recombinant" (rec8B10F8 and rec5F10F175E2) antibodies.

pPMhIgG1 is an mammalian cell expression vector. It contains a sequence encoding the signal peptide of mouse Ig kappa chain, followed by the sequence of the human IgG1 constant region (CH1-3) (SEQ ID NO: 47), cloned between the Nhe I and Not I sites. pPMhIgG1 allows the construction of the full length human IgG1 heavy chain by cloning the variable region (VH) between the Sal I and Nhe I sites. To construct the expression vector for the light chain, the entire light chain sequence is cloned between Sal I and Not I sites. Using this cloning strategy, the secretion of both heavy and light chains is directed by the mouse Ig kappa chain signal peptide (see FIG. 6).

The recombinant antibodies (rec8B10F8 and rec5F10F175E2) were purified from the transfected cells following the above described procedure.

Example 4

In Vitro Characterization of Recombinant mAbs

Determination of the Recombinant mAbs In Vitro Neutralizing Properties

The capacity of the purified recombinant antibodies (rec8B10F8 and rec5F10F175E2) to neutralize Chikungunya virus infection in vitro was analyzed by a neutralization test in 96-wells plates. For comparison purposes, the test was also performed on the originally isolated antibodies (8B10F8 and 5F10F175E2).

4000 plaque forming units (PFU) of Chikungunya virus (A226 and A226V strains, respectively) were incubated for 1 h at 37° C. with 1 µg of antibody (isolated or recombinant). In addition, 1/40 of anti-Chikungunya virus human plasma (isolated from the donor patient) in 100 µl of PBS was used as a positive control, and 1 µg of purified irrelevant human IgG1 HA4 (human IgG1 Ab specific for H5N1 Influenza virus, kindly provided by DSO National Laboratories, Singapore) as a negative control. The mixtures were then added for 1.5 hours to 40,000 HEK 293T cells, which were seeded within 96-wells plates 24 h before. 24 hours after infection, cells were extensively washed and fixed as described above. The infection of Chikungunya virus was assessed by incubating the cells for 1 hour with 100 µl of PBS-1/200 anti-Chikungunya virus human plasma as a primary antibody, followed by an anti-human IgG mouse antibody conjugated to Alexa-488 at 2 µg/ml (Alexa Fluor 488 goat anti-human IgG(H+L), Invitrogen) as a secondary antibody. Fluorescence was analyzed under a fluorescent microscope (×10 magnificence, NIKON ECLIPSE TS 100).

In FIG. 3 is shown the neutralizing activity of the two antibodies isolated from immortalized B cells (8B10F8 and 5F10F175E2) and also the neutralizing activity of the two corresponding recombinant antibodies (rec8B10F8 and rec5F10F175E2). It can be observed that the neutralization potential of the recombinant antibodies is similar to the corresponding B cell-purified antibodies.

Dose-Response Curves of the Recombinant mAbs Against A226 and A226V Strains

Once having demonstrated that the recombinant antibodies have neutralization characteristics similar to those previously shown for the corresponding B cell-purified antibodies (FIG. 3), the recombinant antibodies were titrated against the Chikungunya virus strains (A226 and A226V) as single agents and in combination to obtain neutralization dose-response curves and determine the IC50. The dose-response curves were obtained by Plaque Reduction Assay performed as described above, and the experiments were performed by triplicate. Results are shown in FIG. 4.

The IC50 value of the recombinant antibodies against the A226V strain was estimated between 20 and 80 ng/ml and the IC50 of the recombinant antibodies against the A226 strain was estimated between 200 and 800 ng/ml.

Determination of the Recombinant mAbs Specificity

To determine recombinant mAb specificity, Western Blot analysis was performed on both CHIKV-infected cells and CHIKV particles. For uninfected cell lysate preparation, 12×10$^6$ Vero cells (ATTC CCL-81) were lysed with 1 ml of lysis buffer (PBS-1% Triton X-100, VWR) with Complete Protease Inhibitor Cocktail (Roche). For infected cell lysate preparation, 6×10$^6$ Vero cells were infected with CHIKV (A226 or A226V, respectively) at a MOI of 1 and 24 h after infection the cells were lysed with 1 ml of lysis buffer. For purified viral particles preparation, 40×10$^6$ Vero cells were infected with CHIKV (A226 or A226V, respectively) at a MOI of 0.1 and 2 days after infection the supernatant was harvested, concentrated on Vivaspin-100 kDa columns (Vivaspin20, Sartorius Stedim) and, after having inactivated the virus for 1 h at 56° C., the viral particles were purified by ultracentrifugation (24,000 rpm for 3 h) performed on a OptiPrep™ (Sigma) cushion. 0.5 ml of purified A226 CHIKV viral particles and 1.25 ml of purified A226V CHIKV viral particles were finally obtained.

Figure 5:
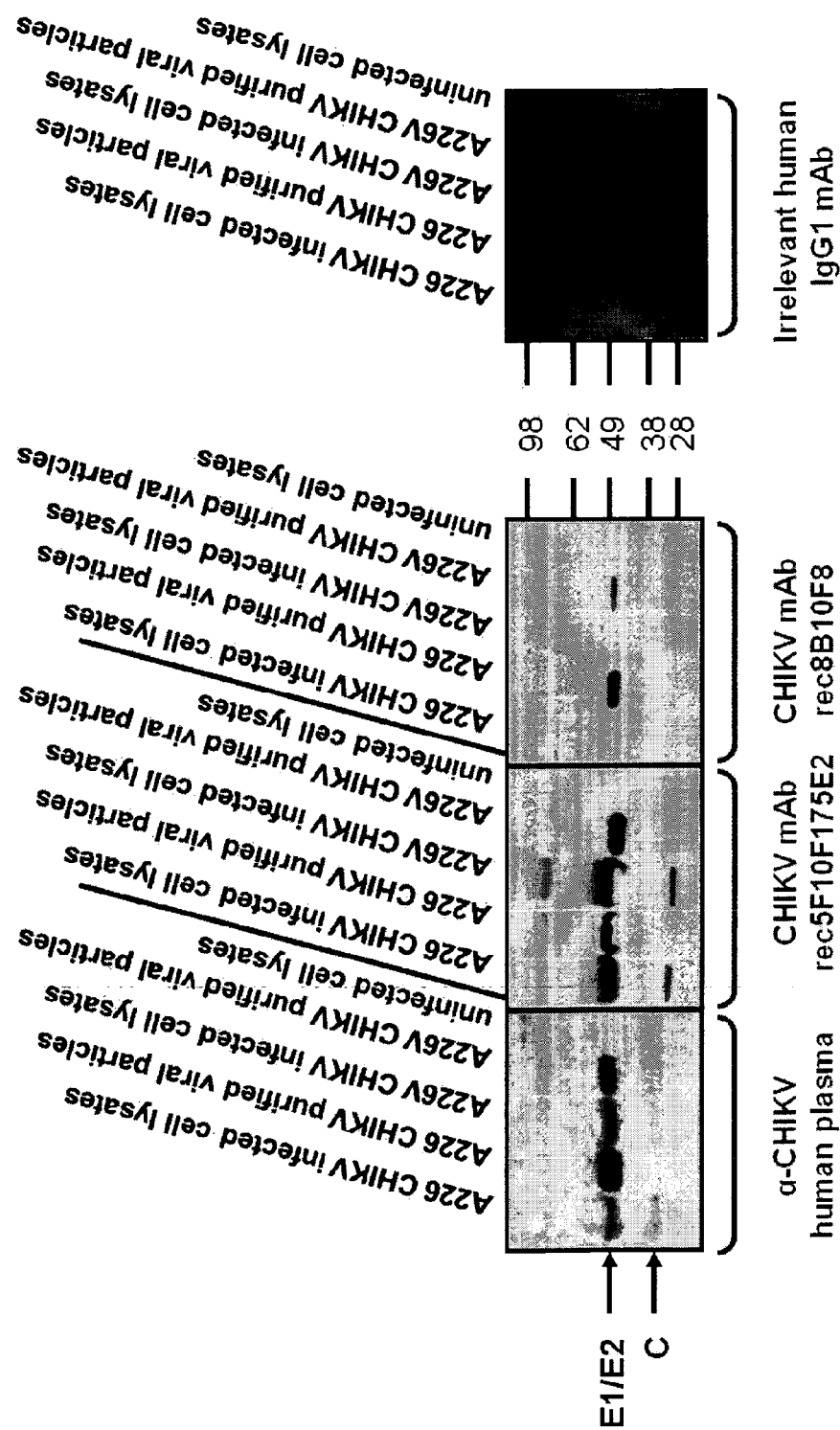
FIG. 5 shows the results obtained by a western blot immunoassay on the recombinant antibodies (rec8B10F8 and rec5F10F175E2) against infected cell lysates and purified viral particles of both A226 and A226V Chikungunya virus strains. (E1/E2) represents the envelope glycoproteins E1 and E2 and (C) represents the viral capsid protein.

15 µl of cell lysates and 1.5 µl of purified viral particles were mixed with NuPAGE® loading buffer (Invitrogen), heated for 5 min at 94° C. and loaded on a NuPAGE® 4-12% Bis-Tris Gel (Invitrogen). The electrophoresis was performed in NuPAGE® MES running buffer (Invitrogen). As molecular weight marker, 5 µl of SeeBlue® marker (Invitrogen) were loaded in parallel. After migration, the samples were electrotransfered onto a hydrophobic polyvinylidene difluoride (PVDF) membrane (Hybond™-P, Amersham, GE Healthcare). The membrane was blocked for 1 h with PBS-milk 5% (cow powdered milk)-Tween 0.05% (Sigma) and probed for 1 h with primary antibody diluted in PBS-milk 0.5%-Tween 0.05% (Sigma) at the following concentrations: 1/250 for the α-CHIKV plasma, 1 µg/ml for CHIKV mAb 5F10F175E2, 20 µg/ml for CHIKV mAb 8B10F8 and 20 µg/ml for irrelevant human IgG1 HA4 (human IgG1 Ab specific for H5N1 Influenza virus, kindly provided by DSO National Laboratories, Singapore). After extensive washing in PBS-Tween (Sigma) 0.1%, the membrane was probed for 1 h with, as a secondary antibody, the Peroxidase-conjugated AffiniPure goat Anti-Human IgG (Fc) (Jackson ImmunoResearch Laboratories) at 40 ng/ml in PBS-milk 0.5%-Tween 0.05%. After extensive washing, the peroxidase activity was detected using ECL substrate solutions (Amersham ECL™ Western Blotting Detection Reagents, GE Healthcare). Western blot immunoassay results (FIG. 5) show that both recombinant antibodies bind to a Chikungunya virus envelope protein (E1 and/or E2). Chikungunya virus envelope glycoproteins E1 and E2 have a similar molecular weight, around 50 kDa (Strauss and Strauss, 1994, Microbiol Rev 58, 491-562). Accordingly, these two proteins cannot be distinguished on a western blot analysis.

SEQUENCE LISTING

<160> NUMBER OF SEQ ID NOS: 53

<210> SEQ ID NO 1
<211> LENGTH: 839
<212> TYPE: DNA
<213> ORGANISM: Artificial
<220> FEATURE:
<223> OTHER INFORMATION: Heavy chain (DNA) of Purified 5F10F175E2

<400> SEQUENCE: 1

```
atggactgga cctggagcgt cctcttcttg gtggcagcag caacaggtgc ccactcccag    60
gtgcaactgg tgcaatctgg gtcggagttg aagaagcctg gggcctcagt gaaggtttcc   120
tgcaaggcct ctggatacac cctcactcgc tatgctatga cttgggtgcg acaggcccct   180
ggacaagggc ttgagtggat gggatggatc aacacctaca ctgggaaccc aacgtatgtc   240
cagggcttca caggacggtt tgtcttctcg ttggacacct ctgtcagcac ggcgtttctg   300
cacatcacca gcctaaaggc tgaggacact gccgtgtatt tctgtgcgag agaagggggc   360 gctcgggtt ttgactactg gggccaggga acctggtca ccgtctcctc agcctccacc     420
aagggcccat cggtcttccc cctggcaccc tcctccaaga gcacctctgg gggcacagcg   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcagcttgg gcacccagac ctacatctgc   660
aacgtgaatc acaagcccag caacaccaag gtggacaaga gagttgagcc caaatcttgt   720
gacaaaactc acacatgccc accgtgccca gcacctgaac tcctgggggg accgtcagtc   780
ttcctcttcc ccccaaaacc caaggacacc ctcatgatct cccggacccc tgaggtcac    839
```

<210> SEQ ID NO 2
<211> LENGTH: 260
<212> TYPE: PRT
<213> ORGANISM: Artificial
<220> FEATURE:
<223> OTHER INFORMATION: Heavy chain (Protein )common to both Purified
      5F10F175E2 and Recombinant 5F10F175E2

<400> SEQUENCE: 2

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Leu Thr Arg Tyr
            20                  25                  30
```

```
Ala Met Thr Trp Val Arg Gln Ala Pro Gly Gln Gly Leu Glu Trp Met
             35                  40                  45
Gly Trp Ile Asn Thr Tyr Thr Gly Asn Pro Thr Tyr Val Gln Gly Phe
 50                  55                  60
Thr Gly Arg Phe Val Phe Ser Leu Asp Thr Ser Val Ser Thr Ala Phe
 65                  70                  75                  80
Leu His Ile Thr Ser Leu Lys Ala Glu Asp Thr Ala Val Tyr Phe Cys
             85                  90                  95
Ala Arg Glu Gly Gly Ala Arg Gly Phe Asp Tyr Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
            165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Arg Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val
            260

<210> SEQ ID NO 3
<211> LENGTH: 711
<212> TYPE: DNA
<213> ORGANISM: Artificial
<220> FEATURE:
<223> OTHER INFORMATION: Light chain (DNA) of Purified 5F10F175E2

<400> SEQUENCE: 3
atggcctggt ctcctctcct cctcactctc ctcgctcact gcacagggtc ctgggcccag      60
tctgtgctga cgcagccgcc ctcagtgtct ggggccccag gcagagggt caccatctcc     120
tgcactggga gcagctccaa catcggggca agtcatgatg tacactggta ccagcagctt     180
cctggaacag cccccacact cctcatctat gttaacagca tcggccctc aggggtccct     240
gaccgattct ctggctccaa gtctggcacc tcagcctccc tggccatcac tgggctccag     300
gctgaggatg aggctgatta ttactgccag tcctatgaca gcaacctgag tggttcggcg     360
gtgttcggcg gagggaccaa gttgaccgtc ctaggtcagc ccaaggctgc ccctcggtc     420
actctgttcc cgccctcctc tgaggagctt caagccaaca ggccacact ggtgtgtctc     480
ataagtgact ctacccgggg agccgtgaca gtggcctgga aggcagatag cagcccgtc     540
aaggcgggag tggagaccac cacaccctcc aaacaaagca acaacaagta cgcggccagc     600
agctacctga gcctgacgcc tgagcagtgg aagtccaca aaagctacag ctgccaggtc     660
acgcatgaag ggagcaccgt ggagaagaca gtggcccct agaatgttc a                711
```

<210> SEQ ID NO 4
<211> LENGTH: 218
<212> TYPE: PRT
<213> ORGANISM: Artificial
<220> FEATURE:
<223> OTHER INFORMATION: Light chain (Protein) common to both Purified
      5F10F175E2 and Recombinant 5F10F175E2

<400> SEQUENCE: 4

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Ser
            20                  25                  30

His Asp Val His Trp Tyr Gln Gln Leu Pro Gly Thr Ala Pro Thr Leu
        35                  40                  45

Leu Ile Tyr Val Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Asn
                85                  90                  95

Leu Ser Gly Ser Ala Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Pro Thr Glu Cys Ser
210                 215

<210> SEQ ID NO 5
<211> LENGTH: 354
<212> TYPE: DNA
<213> ORGANISM: Artificial
<220> FEATURE:
<223> OTHER INFORMATION: VH domain

<400> SEQUENCE: 5
caggtgcaac tggtgcaatc tgggtcggag ttgaagaagc ctggggcctc agtgaaggtt      60
tcctgcaagg cctctggata caccctcact cgctatgcta tgacttgggt gcgacaggcc    120
cctggacaag gcttgagtg gatgggatgg atcaacacct acactgggaa cccaacgtat     180
gtccagggct tcacaggacg gtttgtcttc tcgttggaca cctctgtcag cacggcgttt    240
ctgcacatca ccagcctaaa ggctgaggac actgccgtgt atttctgtgc gagagaaggg    300
ggcgctcggg gttttgacta ctggggccag ggaaccctgg tcaccgtctc ctca           354

<210> SEQ ID NO 6
<211> LENGTH: 118
<212> TYPE: PRT

<213> ORGANISM: Artificial
<220> FEATURE:
<223> OTHER INFORMATION: VH domain

<400> SEQUENCE: 6

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Leu Thr Arg Tyr
            20                  25                  30

Ala Met Thr Trp Val Arg Gln Ala Pro Gly Gln Gly Leu Glu Trp Met
        35                  40                  45

Gly Trp Ile Asn Thr Tyr Thr Gly Asn Pro Tyr Val Gln Gly Phe
    50                  55                  60

Thr Gly Arg Phe Val Phe Ser Leu Asp Thr Ser Val Ser Thr Ala Phe
65                  70                  75                  80

Leu His Ile Thr Ser Leu Lys Ala Glu Asp Thr Ala Val Tyr Phe Cys
                85                  90                  95

Ala Arg Glu Gly Gly Ala Arg Gly Phe Asp Tyr Trp Gly Gln Gly Thr
            100                 105                 110

Leu Val Thr Val Ser Ser
        115

<210> SEQ ID NO 7
<211> LENGTH: 336
<212> TYPE: DNA
<213> ORGANISM: Artificial
<220> FEATURE:
<223> OTHER INFORMATION: VL domain

<400> SEQUENCE: 7
cagtctgtgc tgacgcagcc gccctcagtg tctggggccc cagggcagag ggtcaccatc      60
tcctgcactg ggagcagctc aacatcggg gcaagtcatg atgtacactg gtaccagcag     120
cttcctggaa cagcccccac actcctcatc tatgttaaca gcaatcggcc ctcaggggtc     180
cctgaccgat tctctggctc caagtctggc acctcagcct ccctggccat cactgggctc     240
caggctgagg atgaggctga ttattactgc cagtcctatg acagcaacct gagtggttcg     300
gcggtgttcg gcggagggac caagttgacc gtccta                               336

<210> SEQ ID NO 8
<211> LENGTH: 112
<212> TYPE: PRT
<213> ORGANISM: Artificial
<220> FEATURE:
<223> OTHER INFORMATION: VL domain

<400> SEQUENCE: 8

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Ser
            20                  25                  30

His Asp Val His Trp Tyr Gln Gln Leu Pro Gly Thr Ala Pro Thr Leu
        35                  40                  45

Leu Ile Tyr Val Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Asn
                85                  90                  95

Leu Ser Gly Ser Ala Val Phe Gly Gly Gly Thr Lys Leu Thr Val Leu
            100                 105                 110

<210> SEQ ID NO 9
<211> LENGTH: 15
<212> TYPE: DNA
<213> ORGANISM: Artificial
<220> FEATURE:
<223> OTHER INFORMATION: CDRH1

<400> SEQUENCE: 9
cgctatgcta tgact                                                           15

<210> SEQ ID NO 10
<211> LENGTH: 5
<212> TYPE: PRT
<213> ORGANISM: Artificial
<220> FEATURE:
<223> OTHER INFORMATION: CDRH1

<400> SEQUENCE: 10

Arg Tyr Ala Met Thr
1               5

<210> SEQ ID NO 11
<211> LENGTH: 51
<212> TYPE: DNA
<213> ORGANISM: Artificial
<220> FEATURE:
<223> OTHER INFORMATION: CDRH2

<400> SEQUENCE: 11
tggatcaaca cctacactgg gaacccaacg tatgtccagg gcttcacagg a                    51

<210> SEQ ID NO 12
<211> LENGTH: 17
<212> TYPE: PRT
<213> ORGANISM: Artificial
<220> FEATURE:
<223> OTHER INFORMATION: CDRH2

<400> SEQUENCE: 12

Trp Ile Asn Thr Tyr Thr Gly Asn Pro Thr Tyr Val Gln Gly Phe Thr
1               5                   10                  15
Gly

<210> SEQ ID NO 13
<211> LENGTH: 27
<212> TYPE: DNA
<213> ORGANISM: Artificial
<220> FEATURE:
<223> OTHER INFORMATION: CDRH3

<400> SEQUENCE: 13 gaaggggcg ctcggggttt tgactac                                               27

<210> SEQ ID NO 14
<211> LENGTH: 9
<212> TYPE: PRT
<213> ORGANISM: Artificial
<220> FEATURE:
<223> OTHER INFORMATION: CDRH3

<400> SEQUENCE: 14

Glu Gly Gly Ala Arg Gly Phe Asp Tyr

```
<210> SEQ ID NO 15
<211> LENGTH: 42
<212> TYPE: DNA
<213> ORGANISM: Artificial
<220> FEATURE:
<223> OTHER INFORMATION: CDRL1

<400> SEQUENCE: 15
actgggagca gctccaacat cggggcaagt catgatgtac ac                              42

<210> SEQ ID NO 16
<211> LENGTH: 14
<212> TYPE: PRT
<213> ORGANISM: Artificial
<220> FEATURE:
<223> OTHER INFORMATION: CDRL1

<400> SEQUENCE: 16

Thr Gly Ser Ser Ser Asn Ile Gly Ala Ser His Asp Val His
1               5                   10

<210> SEQ ID NO 17
<211> LENGTH: 21
<212> TYPE: DNA
<213> ORGANISM: Artificial
<220> FEATURE:
<223> OTHER INFORMATION: CDRL2

<400> SEQUENCE: 17
gttaacagca atcggccctc a                                                     21

<210> SEQ ID NO 18
<211> LENGTH: 7
<212> TYPE: PRT
<213> ORGANISM: Artificial
<220> FEATURE:
<223> OTHER INFORMATION: CDRL2

<400> SEQUENCE: 18

Val Asn Ser Asn Arg Pro Ser
1               5

<210> SEQ ID NO 19
<211> LENGTH: 36
<212> TYPE: DNA
<213> ORGANISM: Artificial
<220> FEATURE:
<223> OTHER INFORMATION: CDRL3

<400> SEQUENCE: 19
cagtcctatg acagcaacct gagtggttcg gcggtg                                     36

<210> SEQ ID NO 20
<211> LENGTH: 12
<212> TYPE: PRT
<213> ORGANISM: Artificial
<220> FEATURE:
<223> OTHER INFORMATION: CDRL3

<400> SEQUENCE: 20

Gln Ser Tyr Asp Ser Asn Leu Ser Gly Ser Ala Val
1               5                   10

<210> SEQ ID NO 21
```

<211> LENGTH: 854
<212> TYPE: DNA
<213> ORGANISM: Artificial
<220> FEATURE:
<223> OTHER INFORMATION: Heavy chain (DNA) of Purified 8B10F8

<400> SEQUENCE: 21

```
atgaagcayc tgtggttttt ccttctcctg gtggcagctc ccagatgggt cctgtcccag    60
gtgcagctgc aggagtcggg cccaggactg gtgaagcctt cggagaccct gtccctcacc   120
tgcactgtct ctggtgactc catcagtagt tactcctgga gctggatccg gcagccccca   180
gggaagggac tggagtggat tggttatatc cattacactg ggagcaccaa ctacaacccc   240
tccctcaaga gtcgactcac catatcagta gacgcgtcca agaaccagtt ctccctgaag   300
ctgagctctg tgaccgctgc ggacacggcc gtgtattact gtgcgagaga ttggggggggg   360
tatagcagca gctggaccta cggtatggac gtctggggcc aagggaccac ggtcaccgtc   420
tcctcagcct ccaccaaggg cccatcggtc ttccccctgg cacccctcc caagagcacc   480
tctgggggca gcggccct gggctgcctg gtcaaggact acttccccga accggtgacg   540
gtgtcgtgga actcaggcgc cctgaccagc ggcgtgcaca ccttcccggc tgtcctacag   600
tcctcaggac tctactccct cagcagcgtg gtgaccgtgc cctccagcag cttgggcacc   660
cagacctaca tctgcaacgt gaatcacaag cccagcaaca ccaaggtgga caagagagtt   720
gagcccaaat cttgtgacaa aactcacaca tgcccaccgt gcccagcacc tgaactcctg   780
ggggaccgt cagtcttcct cttcccccca aaacccaagg acaccctcat gatytcccgg   840
accccctgagg tcac                                                    854
```

<210> SEQ ID NO 22
<211> LENGTH: 266
<212> TYPE: PRT
<213> ORGANISM: Artificial
<220> FEATURE:
<223> OTHER INFORMATION: Heavy chain (Protein)of common to both Purified 8B10F8 and Recombinant 8B10F8

<400> SEQUENCE: 22

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Tyr
            20                  25                  30

Ser Trp Ser Trp Ile Arg Gln Pro Pro Gly Lys Gly Leu Glu Trp Ile
        35                  40                  45

Gly Tyr Ile His Tyr Thr Gly Ser Thr Asn Tyr Asn Pro Ser Leu Lys
    50                  55                  60

Ser Arg Leu Thr Ile Ser Val Asp Ala Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Trp Gly Gly Tyr Ser Ser Ser Trp Thr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr
            260                 265

<210> SEQ ID NO 23
<211> LENGTH: 708
<212> TYPE: DNA
<213> ORGANISM: Artificial
<220> FEATURE:
<223> OTHER INFORMATION: Light chain (DNA) of Purified 8B10F8

<400> SEQUENCE: 23
atggacatga gggtcccgc tcagctcctg gggctcctgc tgctctggct cccaggtacc        60
agatgtgaca tccagatgac ccagtctcca tcctccctgt ctgcatctgt aggagacaga      120
gtcaccatca cttgccgggc gagtcagggc attagcaatt ctttagcctg gtatcagcag      180
aaaccaggga aagcccctaa gctcctgctc tatgctgcat ccagattgga aagtggggtc      240
ccatccaggt tcagtggcag tggatctggg acggattaca ctctcaccat cagcagcctg      300
cagcctgaag attttgcaac ttattactgt caacagtatt atagtacccc gtacactttt      360
ggccagggga ccaagctgga gatcaaacga actgtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgt                   708

<210> SEQ ID NO 24
<211> LENGTH: 214
<212> TYPE: PRT
<213> ORGANISM: Artificial
<220> FEATURE:
<223> OTHER INFORMATION: Light chain (Protein) common to both Purified
      8B10F8 and Recombinant 8B10F8

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
```

```
                65                  70                  75                  80
Glu Asp Phe Ala Thr Tyr Tyr Cys Gln Gln Tyr Tyr Ser Thr Pro Tyr
                    85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 25
<211> LENGTH: 369
<212> TYPE: DNA
<213> ORGANISM: Artificial
<220> FEATURE:
<223> OTHER INFORMATION: VH domain of Purified 8B10F8

<400> SEQUENCE: 25
caggtgcagc tgcaggagtc gggcccagga ctggtgaagc cttcggagac cctgtccctc      60
acctgcactg tctctggtga ctccatcagt agttactcct ggagctggat ccggcagccc     120
ccagggaagg gactggagtg gattggttat atccattaca ctgggagcac caactacaac     180
ccctccctca gagtcgact  caccatatca gtagacgcgt ccaagaacca gttctccctg     240
aagctgagct ctgtgaccgc tgcggacacg gccgtgtatt actgtgcgag agattggggg     300
gggtatagca gcagctggac ctacggtatg gacgtctggg gccaagggac cacggtcacc     360
gtctcctca                                                             369

<210> SEQ ID NO 26
<211> LENGTH: 123
<212> TYPE: PRT
<213> ORGANISM: Artificial
<220> FEATURE:
<223> OTHER INFORMATION: VH domain common to both Purified 8B10F8 and
      Recombinant 8B10F8

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
                20                  25                  30

Ser Trp Ser Trp Ile Arg Gln Pro Pro Gly Lys Gly Leu Glu Trp Ile
            35                  40                  45

Gly Tyr Ile His Tyr Thr Gly Ser Thr Asn Tyr Asn Pro Ser Leu Lys
        50                  55                  60

Ser Arg Leu Thr Ile Ser Val Asp Ala Ser Lys Asn Gln Phe Ser Leu
65                  70                  75                  80
```

```
Lys Leu Ser Ser Val Thr Ala Ala Asp Thr Ala Val Tyr Tyr Cys Ala
            85                  90                  95

Arg Asp Trp Gly Gly Tyr Ser Ser Trp Tyr Gly Met Asp Val
        100                 105                 110

Trp Gly Gln Gly Thr Thr Val Thr Val Ser Ser
        115                 120
```

<210> SEQ ID NO 27
<211> LENGTH: 321
<212> TYPE: DNA
<213> ORGANISM: Artificial
<220> FEATURE:
<223> OTHER INFORMATION: VL domain

<400> SEQUENCE: 27

```
gacatccaga tgacccagtc tccatcctcc ctgtctgcat ctgtaggaga cagagtcacc    60
atcacttgcc gggcgagtca gggcattagc aattctttag cctggtatca gcagaaacca   120
gggaaagccc ctaagctcct gctctatgct gcatccagat ggaaagtgg ggtcccatcc    180
aggttcagtg gcagtggatc tgggacggat acactctca ccatcagcag cctgcagcct    240
gaagattttg caacttatta ctgtcaacag tattatagta ccccgtacac ttttggccag   300
gggaccaagc tggagatcaa a                                             321
```

<210> SEQ ID NO 28
<211> LENGTH: 107
<212> TYPE: PRT
<213> ORGANISM: Artificial
<220> FEATURE:
<223> OTHER INFORMATION: VL domain

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Tyr
                85                  90                  95

Thr Phe Gly Gln Gly Thr Lys Leu Glu Ile Lys
        100                 105
```

<210> SEQ ID NO 29
<211> LENGTH: 15
<212> TYPE: DNA
<213> ORGANISM: Artificial
<220> FEATURE:
<223> OTHER INFORMATION: CDRH1

<400> SEQUENCE: 29

```
agttactcct ggagc                                                     15
```

<210> SEQ ID NO 30
<211> LENGTH: 5
<212> TYPE: PRT
<213> ORGANISM: Artificial

<220> FEATURE:
<223> OTHER INFORMATION: CDRH1

<400> SEQUENCE: 30

Ser Tyr Ser Trp Ser
1               5

<210> SEQ ID NO 31
<211> LENGTH: 48
<212> TYPE: DNA
<213> ORGANISM: Artificial
<220> FEATURE:
<223> OTHER INFORMATION: CDRH2 of Purified 8B10F8

<400> SEQUENCE: 31
tatatccatt acactgggag caccaactac aacccctccc tcaagagt                48

<210> SEQ ID NO 32
<211> LENGTH: 16
<212> TYPE: PRT
<213> ORGANISM: Artificial
<220> FEATURE:
<223> OTHER INFORMATION: CDRH2 common to both Purified 8B10F8 and
      Recombinant 8B10F8

<400> SEQUENCE: 32

Tyr Ile His Tyr Thr Gly Ser Thr Asn Tyr Asn Pro Ser Leu Lys Ser
1               5                   10                  15

<210> SEQ ID NO 33
<211> LENGTH: 45
<212> TYPE: DNA
<213> ORGANISM: Artificial
<220> FEATURE:
<223> OTHER INFORMATION: CDRH3

<400> SEQUENCE: 33
gattgggggg ggtatagcag cagctggacc tacggtatgg acgtc                 45

<210> SEQ ID NO 34
<211> LENGTH: 15
<212> TYPE: PRT
<213> ORGANISM: Artificial
<220> FEATURE:
<223> OTHER INFORMATION: CDRH3

<400> SEQUENCE: 34

Asp Trp Gly Gly Tyr Ser Ser Ser Trp Thr Tyr Gly Met Asp Val
1               5                   10                  15

<210> SEQ ID NO 35
<211> LENGTH: 33
<212> TYPE: DNA
<213> ORGANISM: Artificial
<220> FEATURE:
<223> OTHER INFORMATION: CDRL1

<400> SEQUENCE: 35
cgggcgagtc agggcattag caattcttta gcc                              33

<210> SEQ ID NO 36
<211> LENGTH: 11
<212> TYPE: PRT
<213> ORGANISM: Artificial
<220> FEATURE:
<223> OTHER INFORMATION: CDRL1

-continued

<400> SEQUENCE: 36

Arg Ala Ser Gln Gly Ile Ser Asn Ser Leu Ala
1               5                   10

<210> SEQ ID NO 37
<211> LENGTH: 21
<212> TYPE: DNA
<213> ORGANISM: Artificial
<220> FEATURE:
<223> OTHER INFORMATION: CDRL2

<400> SEQUENCE: 37
gctgcatcca gattggaaag t                                            21

<210> SEQ ID NO 38
<211> LENGTH: 7
<212> TYPE: PRT
<213> ORGANISM: Artificial
<220> FEATURE:
<223> OTHER INFORMATION: CDRL2

<400> SEQUENCE: 38

Ala Ala Ser Arg Leu Glu Ser
1               5

<210> SEQ ID NO 39
<211> LENGTH: 27
<212> TYPE: DNA
<213> ORGANISM: Artificial
<220> FEATURE:
<223> OTHER INFORMATION: CDRL3

<400> SEQUENCE: 39
caacagtatt atagtacccc gtacact                                      27

<210> SEQ ID NO 40
<211> LENGTH: 9
<212> TYPE: PRT
<213> ORGANISM: Artificial
<220> FEATURE:
<223> OTHER INFORMATION: CDRL3

<400> SEQUENCE: 40

Gln Gln Tyr Tyr Ser Thr Pro Tyr Thr
1               5

<210> SEQ ID NO 41
<211> LENGTH: 842
<212> TYPE: DNA
<213> ORGANISM: Artificial
<220> FEATURE:
<223> OTHER INFORMATION: Heavy chain (DNA) Recombinant 5F10F175E2

<400> SEQUENCE: 41
atggagacag acacactcct gctatgggta ctgctgctct ggttccagg gtcgactggc     60 caggtgcaac tggtgcaatc tgggtcggag ttgaagaagc ctggggcctc agtgaaggtt   120
tcctgcaagg cctctggata caccctcact cgctatgcta tgacttgggt gcgacaggcc   180
cctggacaag gcttgagtg gatgggatgg atcaacacct acactgggaa cccaacgtat   240
gtccagggct tcacaggacg gtttgtcttc tcgttggaca cctctgtcag cacggcgttt   300
ctgcacatca ccagcctaaa ggctgaggac actgccgtgt atttctgtgc gagagaaggg   360
ggcgctcggg gttttgacta ctgggggccag ggaaccctgg tcaccgtctc ctcagcctcc   420

| | |
|---|---|
| accaagggcc catcggtctt cccgctagca ccctcctcca agagcacctc tgggggcaca | 480 |
| gcggccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct tgggcaccca gacctacatc | 660 |
| tgcaacgtga atcacaagcc cagcaacacc aaggtggaca agagagttga gcccaaatct | 720 |
| tgtgacaaaa ctcacacatg cccaccgtgc ccagcacctg aactcctggg gggaccgtca | 780 |
| gtcttcctct tccccccaaa acccaaggac accctcatga tctcccggac ccctgaggtc | 840 |
| ac | 842 |

<210> SEQ ID NO 42
<211> LENGTH: 714
<212> TYPE: DNA
<213> ORGANISM: Artificial
<220> FEATURE:
<223> OTHER INFORMATION: Light chain (DNA) of Recombinant 5F10F175E2

<400> SEQUENCE: 42

| | |
|---|---|
| atggagacag acacactcct gctatgggta ctgctgctct ggttccagg gtcgactggc | 60 |
| cagtctgtgc tgacgcagcc gccctcagtg tctggggccc cagggcagag ggtcaccatc | 120 |
| tcctgcactg ggagcagctc caacatcggg gcaagtcatg atgtacactg gtaccagcag | 180 |
| cttcctggaa cagcccccac actcctcatc tatgttaaca gcaatcggcc ctcaggggtc | 240 |
| cctgaccgat tctctggctc caagtctggc acctcagcct ccctggccat cactgggctc | 300 |
| caggctgagg atgaggctga ttattactgc cagtcctatg acagcaacct gagtggttcg | 360 |
| gcggtgttcg gcggagggac caagttgacc gtcctaggtc agcccaaggc tgccccctcg | 420 |
| gtcactctgt tcccgccctc ctctgaggag cttcaagcca caaggccac actggtgtgt | 480 |
| ctcataagtg acttctaccc gggagccgtg acagtggcct ggaaggcaga tagcagcccc | 540 |
| gtcaaggcgg gagtggagac caccacaccc tccaaacaaa gcaacaacaa gtacgcggcc | 600 |
| agcagctacc tgagcctgac gcctgagcag tggaagtccc acaaaagcta cagctgccag | 660 |
| gtcacgcatg aagggagcac cgtggagaag acagtggccc ctacagaatg ttca | 714 |

<210> SEQ ID NO 43
<211> LENGTH: 857
<212> TYPE: DNA
<213> ORGANISM: Artificial
<220> FEATURE:
<223> OTHER INFORMATION: Heavy chain (DNA) of Recombinant 8B10F8

<400> SEQUENCE: 43

| | |
|---|---|
| atggagacag acacactcct gctatgggta ctgctgctct ggttccagg gtcgactggc | 60 |
| caggtgcagc tgcaggagtc gggcccagga ctggtgaagc cttcggagac cctgtccctc | 120 |
| acctgcactg tctctggtga ctccatcagt agttactcct ggagctggat ccggcagccc | 180 |
| ccagggaagg gactggagtg gattggttat atccattaca ctgggagcac caactacaac | 240 |
| ccctccctca gagccgact caccatatca gtagacgcgt ccaagaacca gttctccctg | 300 |
| aagctgagct ctgtgaccgc tgcggacacg gccgtgtatt actgtgcgag agattggggg | 360 |
| gggtatagca gcagctggac ctacggtatg gacgtctggg gccaagggac cacggtcacc | 420 |
| gtctcctcag cctccaccaa gggcccatcg gtcttcccgc tagcaccctc ctccaagagc | 480 |
| acctctgggg gcacagcggc cctgggctgc ctggtcaagg actacttccc cgaaccggtg | 540 |
| acggtgtcgt ggaactcagg cgccctgacc agcggcgtgc acaccttccc ggctgtccta | 600 |

```
cagtcctcag gactctactc cctcagcagc gtggtgaccg tgccctccag cagcttgggc    660
acccagacct acatctgcaa cgtgaatcac aagcccagca acaccaaggt ggacaagaga    720
gttgagccca atcttgtga caaaactcac acatgcccac cgtgcccagc acctgaactc    780 ctgggggggac cgtcagtctt cctcttcccc ccaaaaccca aggacaccct catgatytcc    840
cggacccctg aggtcac                                                   857
```

<210> SEQ ID NO 44
<211> LENGTH: 702
<212> TYPE: DNA
<213> ORGANISM: Artificial
<220> FEATURE:
<223> OTHER INFORMATION: Light chain (DNA) of Recombinant 8B10F8

<400> SEQUENCE: 44

```
atggagacag acacactcct gctatgggta ctgctgctct gggttccagg gtcgactggc     60
gacatccaga tgacccagtc tccatcctcc ctgtctgcat ctgtaggaga cagagtcacc    120
atcacttgcc gggcgagtca gggcattagc aattctttag cctggtatca gcagaaacca    180
gggaaagccc ctaagctcct gctctatgct gcatccagat tggaaagtgg ggtcccatcc    240
aggttcagtg gcagtggatc tgggacggat tacactctca ccatcagcag cctgcagcct    300
gaagattttg caactyatta ctgtcaacag tattatagta ccccgtacac ttttggccag    360
gggaccaagc tggagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gt                       702
```

<210> SEQ ID NO 45
<211> LENGTH: 369
<212> TYPE: DNA
<213> ORGANISM: Artificial
<220> FEATURE:
<223> OTHER INFORMATION: VH domain(DNA) of Recombinant 8B10F8

<400> SEQUENCE: 45

```
caggtgcagc tgcaggagtc gggcccagga ctggtgaagc cttcggagac cctgtccctc     60
acctgcactg tctctggtga ctccatcagt agttactcct ggagctggat ccggcagccc    120
ccagggaagg gactggagtg gattggttat atccattaca ctgggagcac caactacaac    180
ccctccctca gagccgact caccatatca gtagacgcgt ccaagaacca gttctccctg    240
aagctgagct ctgtgaccgc tgcggacacg gccgtgtatt actgtgcgag agattggggg    300
gggtatagca gcagctggac ctacggtatg gacgtctggg gccaagggac cacggtcacc    360
gtctcctca                                                            369
```

<210> SEQ ID NO 46
<211> LENGTH: 48
<212> TYPE: DNA
<213> ORGANISM: Artificial
<220> FEATURE:
<223> OTHER INFORMATION: VH domain(DNA) of Recombinant 8B10F8

<400> SEQUENCE: 46
tatatccatt acactgggag caccaactac aacccctccc tcaagagc        48

Figure 6:
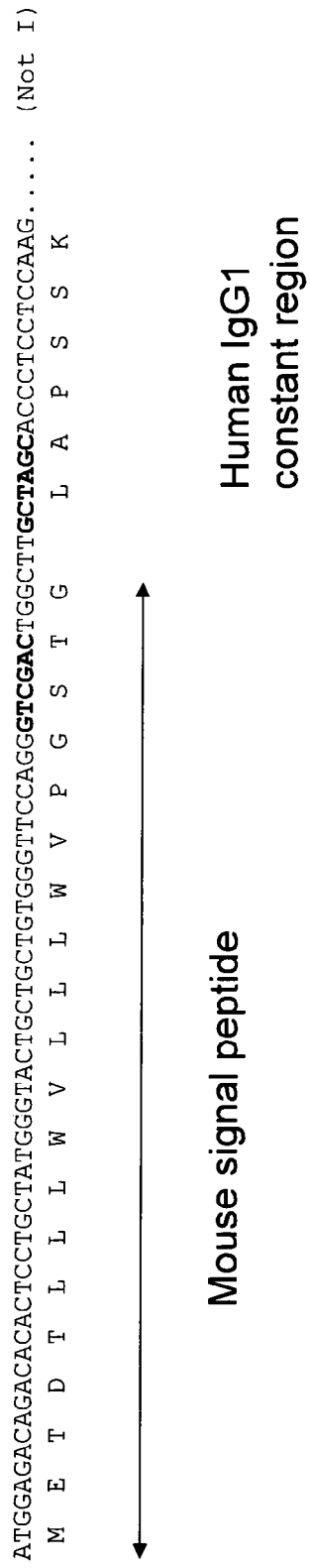
FIG. 6 shows the mouse signal peptide of Ig kappa chain (SEQ ID No. 48), followed by the first nucleotides/amino acids of the human IgG1 constant region sequence (SEQ ID No. 49). The Sal I and Nhe I sites are shown in bold case.

<210> SEQ ID NO 47
<211> LENGTH: 81
<212> TYPE: DNA
<213> ORGANISM: Artificial
<220> FEATURE:
<223> OTHER INFORMATION: Mouse signal peptide followed by human IgG1
      constant region (Figure 6)

<400> SEQUENCE: 47
atggagacag acacactcct gctatgggta ctgctgctgt gggttccagg gtcgactggc        60
ttgctagcac cctcctccaa g        81

<210> SEQ ID NO 48
<211> LENGTH: 20
<212> TYPE: PRT
<213> ORGANISM: Artificial
<220> FEATURE:
<223> OTHER INFORMATION: Mouse signal peptide (Figure 6)

<400> SEQUENCE: 48

Met Glu Thr Asp Thr Leu Leu Leu Trp Val Leu Leu Leu Trp Val Pro
1               5                   10                  15

Gly Ser Thr Gly
            20

<210> SEQ ID NO 49
<211> LENGTH: 6
<212> TYPE: PRT
<213> ORGANISM: Artificial
<220> FEATURE:
<223> OTHER INFORMATION: Human IgG1 constant region (Figure 6)

<400> SEQUENCE: 49

Leu Ala Pro Ser Ser Lys
1               5

<210> SEQ ID NO 50
<211> LENGTH: 280
<212> TYPE: PRT
<213> ORGANISM: Artificial
<220> FEATURE:
<223> OTHER INFORMATION: Heavy chain variable domain (VH) and a partial
      region of the Constant Heavy 1 (CH1) domain of 5F10F175E2
      (figure 2A)

<400> SEQUENCE: 50

Met Asp Trp Thr Trp Ser Val Leu Phe Leu Val Ala Ala Thr Gly
1               5                   10                  15

Ala His Ser Gln Val Gln Leu Val Gln Ser Gly Ser Glu Leu Lys Lys
            20                  25                  30

Pro Gly Ala Ser Val Lys Val Ser Cys Lys Ala Ser Gly Tyr Thr Leu
        35                  40                  45

Thr Arg Tyr Ala Met Thr Trp Val Arg Gln Ala Pro Gly Gln Gly Leu
    50                  55                  60

Glu Trp Met Gly Trp Ile Asn Thr Tyr Thr Gly Asn Pro Thr Tyr Val
65                  70                  75                  80

Gln Gly Phe Thr Gly Arg Phe Val Phe Ser Leu Asp Thr Ser Val Ser
                85                  90                  95

Thr Ala Phe Leu His Ile Thr Ser Leu Lys Ala Glu Asp Thr Ala Val
                100                 105                 110

```
Tyr Phe Cys Ala Arg Glu Gly Ala Arg Gly Phe Asp Tyr Trp Gly
            115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr
        275                 280

<210> SEQ ID NO 51
<211> LENGTH: 237
<212> TYPE: PRT
<213> ORGANISM: Artificial
<220> FEATURE:
<223> OTHER INFORMATION: sequence of whole light chain of 5F10F175E2

<400> SEQUENCE: 51

Met Ala Trp Ser Pro Leu Leu Leu Thr Leu Leu Ala His Cys Thr Gly
1               5                   10                  15

Ser Trp Ala Gln Ser Val Leu Thr Gln Pro Pro Ser Val Ser Gly Ala
            20                  25                  30

Pro Gly Gln Arg Val Thr Ile Ser Cys Thr Gly Ser Ser Ser Asn Ile
        35                  40                  45

Gly Ala Ser His Asp Val His Trp Tyr Gln Gln Leu Pro Gly Thr Ala
    50                  55                  60

Pro Thr Leu Leu Ile Tyr Val Asn Ser Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Leu Gln Ala Glu Asp Glu Ala Asp Tyr Tyr Cys Gln Ser Tyr
            100                 105                 110

Asp Ser Asn Leu Ser Gly Ser Ala Val Phe Gly Gly Gly Thr Lys Leu
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190
```

```
Ser Asn Asn Lys Tyr Ala Ala Ser Ser Tyr Leu Ser Leu Thr Pro Glu
        195                 200                 205

Gln Trp Lys Ser His Lys Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 52
<211> LENGTH: 285
<212> TYPE: PRT
<213> ORGANISM: Artificial
<220> FEATURE:
<223> OTHER INFORMATION: Heavy chain variable domain (VH) and a partial
      region of the Constant Heavy 1 (CH1) domain of 8B10F8 antibody

<400> SEQUENCE: 52

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Asp Ser Ile
        35                  40                  45

Ser Ser Tyr Ser Trp Ser Trp Ile Arg Gln Pro Pro Gly Lys Gly Leu
    50                  55                  60

Glu Trp Ile Gly Tyr Ile His Tyr Thr Gly Ser Thr Asn Tyr Asn Pro
65                  70                  75                  80

Ser Leu Lys Ser Arg Leu Thr Ile Ser Val Asp Ala Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Trp Gly Gly Tyr Ser Ser Ser Trp Thr Tyr Gly
        115                 120                 125

Met Asp Val Trp Gly Gln Gly Thr Thr Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr
        275                 280                 285

<210> SEQ ID NO 53
<211> LENGTH: 236
<212> TYPE: PRT
<213> ORGANISM: Artificial
```

```
-continued

<220> FEATURE:
<223> OTHER INFORMATION: Whole light chain of 8B10F8 antibody

<400> SEQUENCE: 53

Met Asp Met Arg Val Pro Ala Gln Leu Leu Gly Leu Leu Leu Leu Trp
1               5                   10                  15

Leu Pro Gly Thr Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Asn Ser Leu Ala Trp Tyr Gln Gln Lys Pro Gly Lys
    50                  55                  60

Ala Pro Lys Leu Leu Leu Tyr Ala Ala Ser Arg Leu Glu Ser Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Thr Tyr Tyr Cys Gln Gln
            100                 105                 110

Tyr Tyr Ser Thr Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

The invention claimed is:

1. An isolated antibody or antigen binding fragment thereof, wherein said antibody or antigen binding fragment thereof comprises a heavy chain amino acid sequence that comprises the CDRH1 depicted as SEQ ID NO: 30, the CDRH2 depicted as SEQ ID NO: 32, and the CDRH3 depicted as SEQ ID NO: 34, and a light chain amino acid sequence that comprises the CDRL1 depicted as SEQ ID NO: 36, the CDRL2 depicted as SEQ ID NO: 38, and the CDRL3 depicted as SEQ ID NO: 40, wherein said antibody or antigen binding fragment thereof comprises a variant Fc region that has been molecularly engineered by the alteration of one or more amino acids relative to naturally occurring Fc regions.

2. The isolated antibody or antigen binding fragment thereof of claim 1, comprising a heavy chain amino acid sequence which comprises the VH domain amino acid sequence depicted as SEQ ID NO: 26, and/or a light chain amino acid sequence that comprises the VL domain amino acid sequence depicted as SEQ ID NO: 28.

3. The isolated antibody or antigen binding fragment thereof of claim 1, comprising the VH domain amino acid sequence of SEQ ID NO: 26 and the VL domain amino acid sequence of SEQ ID NO: 28.

4. The isolated antibody or antigen binding fragment thereof of claim 1, wherein said antibody or antigen binding fragment thereof binds to Chikungunya Virus.

5. An immunoconjugate of the antibody or antigen binding fragment thereof of claim 1, wherein said antibody or antigen binding fragment thereof is coupled to at least one labeling and/or effector group.

6. An isolated nucleic acid molecule comprising a nucleic acid sequence encoding the antibody or antigen binding fragment thereof of claim 1.

7. A vector comprising the nucleic acid molecule of claim 6.

8. An isolated host cell comprising the nucleic acid molecule of claim 6.

9. A pharmaceutical composition comprising the isolated antibody or antigen binding fragment thereof of claim 1, and a pharmaceutically acceptable carrier, diluent or adjuvant.

10. A kit comprising the isolated antibody or antigen binding fragment thereof of claim 1.

11. A method for inhibiting the infection of Chikungunya virus comprising administering an effective amount of the isolated antibody or antigen binding fragment thereof of claim 1.

12. The isolated antigen binding fragment thereof of claim 1, which comprises a heavy chain amino acid sequence that comprises the CDRH1 depicted as SEQ ID NO: 30, the CDRH2 depicted as SEQ ID NO: 32, and the CDRH3 depicted as SEQ ID NO: 34, and a light chain amino acid sequence that comprises the CDRL1 depicted as SEQ ID NO: 36, the CDRL2 depicted as SEQ ID NO: 38, and the CDRL3 depicted as SEQ ID NO: 40.

13. The isolated antigen binding fragment thereof of claim 12, wherein the antigen binding fragment is selected from the group consisting of: a Fab fragment, a Fab' fragment, a F(ab')2 fragment, a Fv fragment, a diabody and single chain antibody molecule.

* * * * *